United States Patent [19]
Sabara et al.

[11] Patent Number: 6,086,880
[45] Date of Patent: Jul. 11, 2000

[54] ROTAVIRUS PEPTIDE COMPOSITIONS AND METHODS OF USE

[75] Inventors: Marta Iris Johanna Sabara; Patrick John Frenchick, both of Rochester, N.Y.; Andrew Allan Potter, Saskatoon, Canada; Mohammad Khalid Ijaz, Saskatoon, Canada; James Elton Gilchrist, Saskatoon, Canada; Mark J. Redmond, Saskatoon, Canada

[73] Assignee: The University of Saskatchewan, Saskatchewan, Canada

[21] Appl. No.: 08/089,397

[22] Filed: Jul. 7, 1993

Related U.S. Application Data

[63] Continuation of application No. 07/661,859, Feb. 27, 1991, abandoned, which is a continuation-in-part of application No. 07/626,041, Dec. 10, 1990, abandoned, which is a continuation-in-part of application No. 07/552,350, Jul. 12, 1990, abandoned, which is a continuation of application No. 07/241,761, Sep. 7, 1988, abandoned, which is a continuation of application No. 06/903,325, Sep. 3, 1986, abandoned, which is a continuation-in-part of application No. 06/813,661, Dec. 26, 1985, abandoned.

[51] Int. Cl.[7] .......................... A61K 39/15; A61K 38/04; A61K 38/08; A61K 38/10
[52] U.S. Cl. .................................. 424/186.1; 424/193.1; 424/196.11; 424/215.1; 530/324; 530/325; 530/326; 530/327; 530/328; 530/350; 530/402; 530/403
[58] Field of Search ..................... 530/324, 325, 530/326, 327, 328, 350, 402, 403, 806, 807; 424/88, 89, 186.1, 193.1, 196.11, 215.1

[56] References Cited

U.S. PATENT DOCUMENTS

| | | | |
|---|---|---|---|
| 4,190,645 | 2/1980 | Almeida | 424/89 |
| 4,474,757 | 10/1984 | Arnon et al. | 424/88 |
| 4,591,552 | 5/1986 | Neurath | 530/324 |
| 4,629,783 | 12/1986 | Cosand | 530/324 |
| 4,704,275 | 11/1987 | Wyatt et al. | 424/89 |
| 4,737,487 | 4/1988 | Watts et al. | 514/15 |
| 5,071,651 | 12/1991 | Sabara et al. | 424/89 |

FOREIGN PATENT DOCUMENTS

| | | |
|---|---|---|
| 0114759 | 8/1984 | European Pat. Off. . |
| 0117657 | 9/1984 | European Pat. Off. . |
| 10235391 | 9/1987 | European Pat. Off. . |
| 0259149 | 3/1988 | European Pat. Off. . |
| WO85/05122 | 11/1985 | WIPO . |

OTHER PUBLICATIONS

Redmond et al., (1991) *Molecular Immunology* 28(3):269–278.
Frenchick et al., in *Applied Virology Research*, 1988, vol. 1, Edited by Edouard Kurstak et al., (Plenum Publishing Corporation), pp. 141–151.
Ijaz et al., (1991) *Journal of Virology* 65(6):3106–3113.
Sabara et al., *J. Virol.* (1985) 53(1):58–66.
Estes et al., *Microbiol. Rev.* (1989) 53:410–449.
Gunn et al., *J. Virol.* (1985) 54(3):791–797.
Estes et al., *Nucleic Acids Res.* (1984) 12(4):1875–1887.
Woode et al., *Viral Immunol.* (1989) 2(2):127–132.
Gouvea et al., *J. Gen. Virol.* (1986) 67:577–581.
Estes et al. *Immunol. Invest.* (1989) 18:571–581.
Gilbert et al., *Virus Res.* (1987) 7:49–67.
Greenberg et al., *J. Gen. Virol.* (1983) 64:313–320.
Greenberg et al., *J. Virol.* (1983) 47(2):267–275.
Lazdins et al., *J. Virol.* (1985) 56(1):317–319.
Glass et al., *Virology* (1985) 141:292–298.
Brown et al., *Bio/Technology* (1985) 3:445–448.
Bittle et al., *Nature* (1982) 298:30–33.
Emini et al., *Nature* (1983) 304:699–703.
Richardson et al., *J. Virol.* (1994) 51(3):860–862.
Lopez et al., *Virology* (1985) 144:11–19.
Clark et al., *J. Virology* (1981) 39(3):816–822.
Sabara et al., *J. Virol.* (1985) 56(3):1037–1040.
Cruse et al.; *Illustrated Dictionary of Immunology*, CRC Press, 1995.
Woode et al., Viral Immunology, vol. 2, No. 2, pp. 127–132 (1989).
Goodman, Basic & Clinical Immunology, Fudenberg et al. (ed.), Lange Medical Publications, Los Altos, California, pp. 32–40 (1976).
Rudinger, Peptide Hormones, Parson (Ed.) U Park Press, Baltimore, pp. 1–7 (1976).
Cram et al., Organic Chemistry, 2nd Edition, McGraw–Hill Book Company, New York, pp. 607–613 (1964).

*Primary Examiner*—Robert D. Budens
*Attorney, Agent, or Firm*—Morrison & Foerster LLP

[57] ABSTRACT

A number of subunits of various rotaviral proteins have been shown to be useful in diagnosis, therapy, and prevention of rotaviral infection. Specifically, the subunits represented by positions 40–60 of VP6, 232–255 and 240–248 of VP4, and 247–259 and 275–295 of VP7 are thus useful. Furthermore, the VP4 subunits have therapeutic value in competing with the native viral protein in an essential step in infection.

39 Claims, 10 Drawing Sheets

FIGURE 1  Amino acid sequence of rotavirus VP7 glycoprotein  (The 14K polypeptide is shown in the box.)

FIGURE 2  AMINO ACID SEQUENCE OF ROTAVIRUS VP4 PROTEIN

```
C486 (bovine)  1   MASLIYROLL TNSYTVELSD EIQEIGSTET QNVTVNPGPF AQTNYASVNW GPGETNDSTT
SA-11(simian)  1         LIYROLL TNSYTVELSD EIQEIGSTET QNVTVNPGPF AQTNYAPVNW GPGETNDSTT 61   VEPVLDGPYQ PTTFNPPVSY WMLLAPTNAG VVDQGTNNTN RWLATILIKP NVQQVERTYT
              61   VEPVLDGPYQ PTTFNPPVSY WMLLAPTNAG VVVEGTNNTN RWLATILIEP NVQQVERTYT 121   LFGQQVQVTV SNDSQTKWKF VDLSKQTQDG NYSQNGPLLS TPKLYGVMKH GGKIYTYNGE
             121   LFGQQVQVTV SNDSQTKWKF VDLSKQTQDG NYSQNGSLLS TPKLYGVMKH GGKIYTYNGE 181   TPNATTGYYS TTNFDTVNMT AYCDFYIIPL AQEAKCTEYI NNGLPPIQNT RNIVPVSIVS
             181   TPNANTGYYS TTNFDTVNMT AYCDFYIIPL AQEAKCTEYI NNGLPPIQNT RNIVPVSIVS 241   RNIVYTRAQP NQDIVVSKTS LWKEMQYNRD IVIRFKFANS IIKSGGLGYK WSEVSFKPAN
             241   RNIVYTRAQP NQDIVVSKTS LWKEMQYVRD IVIRFKFANS IIKSGGLGYK WSEVSFKPAF 301   YQYTYTRDGE EVTAHTTCSV NGINDFNYNG GSLPTDFVIS KYEVIKENSF VYIDYWDDSQ
             301   YQYTYTRDGE EVTAHTTCSV NGVNDFNYNG GSLPTDFVIS KYEVIKENSF VYIDYWDDSQ 361   AFRNMVYVRS LAADLNSVMC TGGDYSFAIP VGNYPVMTGG AVSLHSAGVT LSTQFTDFVS
             361   AFRNMVYVRS LAADLNSVMC TGGDYSFALP VGNYPVMTGG AVSLHSAGVT LSTQFTDFVS 421   LNSLRFRFRL SVEEPPFSIL RTRVSGLYGL PAAKPNNSQE YYEIAGRFSL ISLVPSNDDY
             421   LNSLRFRFRL SVEEPPFSIL RTRVSGLYGL PAAKPNNSQE YYEIAGRFSL ISLVPLNDDY 481   QTPIINSVTV RQDLERQLGE LRDEFNNLSQ QIAMSQLIDL ALLPLDMFSM FSGIKSTIDA
             481   QTPIMNSVTV RQDLERQLGE LRDEFNNLSQ QIAMSQLIDL ALLPLDMFSM FSGIKSTIDA 541   AKSMATNVMK RFKKSSLANS VSTLTDSLSD AASSISRSAS VRSVSSTASA WTEVSNITSD
             541   AKSMATHVMK RFKKSSLANS VSTLTDSLSD AASSISRSAS VRSVSSTASA WTEVSNIASD 601   INVTTSSIST QTSTISRRLR LKEMATQTDG MNFDDISAAV LKTKIDKSTQ LNTNTLPEIV
             601   INVTTSSIST QTSTISRRLR LKEMATQTDG MNFDDISAAV LKTKIDKSTQ LNTNTLPEIV 661   TEASEKFIPN RAYRVIKDDE VLEASTDGKY FAYKVETILK RFRSMYKFAD LVTDSPVISA
             661   TEASEKFIPN RAYRVIKDDE VLEASIDGKY FAYKVETFEE IPFDVQKFAD LVTDSPVISA 721   IIDFKTLKNL NDNYGISRQQ ALNLLRSDPR VLREFINQDN PIIRNRIESL IMQCRL
             721   IIDFKTLKNL NDNYGISRQQ ALNLLRSDPR
```

Nucleic Acids Research

|  |  |
|---|---|
| MET ASP VAL LEU TYR SER LEU SER LYS THR LEU LYS ASP ALA | 14 |
| 5'-GGCTTTTAAACGAAGTCTTCAAC ATG GAT GTC CTA TAC TCT TTG TCA AAG ACT CTT AAA GAC GCT | 65 |
| ARG ASP LYS ILE VAL GLU GLY THR LEU TYR SER ASN VAL SER ASP LEU ILE GLN GLN PHE | 34 |
| AGA GAC AAA ATT GTC GAA GGC ACA TTG TAT TCT AAC GTG AGT GAT CTA ATT CAA CAA TTT | 125 |
| ASN GLN MET ILE ILE THR MET ASN GLY ASN GLU PHE GLN THR GLY GLY ILE GLY ASN LEU | 54 |
| AAT CAA ATG ATA ATT ACT ATG AAT GGA AAT GAA TTT CAA ACT GGA GGA ATC GGT AAT TTG | 185 |
| PRO ILE ARG ASN TRP ASN PHE ASN PHE GLY LEU LEU GLY THR THR LEU LEU ASN LEU ASP | 74 |
| CCA ATT AGA AAC TGG AAT TTT AAT TTC GGG TTA CTT GGA ACA ACT TTG CTG AAC TTA GAC | 245 |
| ALA ASN TYR VAL GLU THR ALA ARG ASN THR ILE ASP TYR PHE VAL ASP PHE VAL ASP ASN | 94 |
| GCT AAT TAT GTT GAA ACG GCA AGA AAT ACA ATT GAT TAT TTC GTG GAT TTT GTA GAC AAT | 305 |
| VAL CYS MET ASP GLU MET VAL ARG GLU SER GLN ARG ASN GLY ILE ALA PRO GLN SER ASP | 114 |
| GTA TGC ATG GAT GAG ATG GTT AGA GAA TCA CAA AGG AAC GGA ATT GCA CCT CAA TCA GAC | 365 |
| SER LEU ARG LYS LEU SER ALA ILE LYS PHE LYS AGR ILE ASN PHE ASP ASN SER SER GLU | 134 |
| TCG CTA AGA AAG CTG TCA GCC ATT AAA TTC AAA AGA ATA AAT TTT GAT AAT TCG TCG GAA | 425 |
| TYR ILE GLU ASN TRP ASN LEU GLN ASN ARG ARG GLN ARG THR GLY PHE THR PHE HIS LYS | 154 |
| TAC ATA GAA AAC TGG AAT TTG CAA AAT AGA AGA CAG AGG ACA GGT TTC ACT TTT CAT AAA | 485 |
| PRO ASN ILE PHE PRO TYR SER ALA SER PHE THR LEU ASN ARG SER GLN PRO ALA HIS ASP | 174 |
| CCA AAC ATT TTT CCT TAT TCA GCA TCA TTT ACA CTA AAT AGA TCA CAA CCC GCT CAT GAT | 545 |
| ASN LEU MET GLY THR MET TRP LEU ASN ALA GLY SER GLU ILE GLN VAL ALA GLY PHE ASP | 194 |
| AAT TTG ATG GGC ACA ATG TGG TTA AAC GCA GGA TCG GAA ATT CAA GTC GCT GGA TTT GAC | 605 |
| TYR SER CYS ALA ILE ASN ALA PRO ALA ASN ILE GLN GLN PHE GLU HIS ILE VAL PRO LEU | 214 |
| TAC TCA TGT GCT ATT AAC GCA CCA GCC AAT ATA CAA CAA TTT GAG CAT ATT GTG CCA CTC | 665 |
| ARG ARG VAL LEU THR THR ALA THR ILE THR LEU LEU PRO ASP ALA GLU ARG PHE SER PHE | 234 |
| CGA AGA GTG TTA ACT ACA GCT ACG ATA ACT CTT CTA CCA GAC GCG GAA AGG TTT AGT TTT | 725 |
| PRO ARG VAL ILE ASN SER ALA ASP GLY ALA THR THR TRP PHE PHE ASN PRO VAL ILE LEU | 254 |
| CCA AGA GTG ATC AAT TCA GCT GAC GGG GCA ACT ACA TGG TTT TTC AAC CCA GTG ATT CTC | 785 |
| ARG PRO ASN ASN VAL GLU VAL GLU PHE LEU LEU ASN GLY GLN ILE ILE ASN THR TYR GLN | 274 |
| AGG CCG AAT AAC GTT GAA GTG GAG TTT CTA TTG AAT GGA CAG ATA ATA AAC ACT TAT CAA | 845 |
| ALA ARG PHE GLY THR ILE VAL ALA ARG ASN PHE ASP THR ILE ARG LEU SER PHE GLN LEU | 294 |
| GCA AGA TTT GGA ACT ATC GTA GCT AGA AAT TTT GAT ACT ATT AGA CTA TCA TTC CAG TTA | 905 |
| MET ARG PRO PRO ASN MET THR PRO ALA VAL ALA VAL LEU PHE PRO ASN ALA GLN PRO PHE | 314 |
| ATG AGA CCA CCA AAC ATG ACA CCA GCA GTA GCA GTA CTA TTC CCG AAT GCA CAG CCA TTC | 965 |
| GLU HIS HIS ALA THR VAL GLY LEU THR LEU ARG ILE GLU SER ALA VAL CYS GLU SER VAL | 334 |
| GAA CAT CAT GCA ACA GTG GGA TTG ACA CTT AGA ATT GAG TCT GCA GTT TGT GAG TCT GTA | 1025 |
| LEU ALA ASP ALA SER GLU THR LEU LEU ALA ASN VAL THR SER VAL ARG GLN GLU TYR ALA | 354 |
| CTC GCC GAT GCA AGT GAA ACT CTA TTA GCA AAT GTA ACA TCC GTT AGG CAA GAG TAC GCA | 1085 |
| ILE PRO VAL GLY PRO VAL PHE PRO PRO GLY MET ASN TRP THR ASP LEU ILE THR ASN TYR | 374 |
| ATA CCA GTT GGA CCA GTC TTT CCA CCA GGT ATG AAC TGG ACT GAT TTA ATC ACC AAT TAT | 1145 |
| SER PRO SER ARG GLU ASP ASN LEU GLN ARG VAL PHE THR VAL ALA SER ILE ARG SER MET | 394 |
| TCA CCG TCT AGG GAG GAC AAT TTG CAA CGC GTA TTT ACA GTG GCT TCC ATT AGA AGC ATG | 1205 |
| LEU ILE LYS ⊗⊗⊗ | 397 |
| CTC ATT AAA TGA GGACCAAGCTAACAACTTGGTATCCAACTTTGGTGAGTATGTAGCTATATCAAGCTGTTTGAA | 1280 |
| CTCTGTAAGTAAGGATGCGTATACGCATTCGCTACACTGAGTTAATCACTCTGATGGTATAGTGAGAGGATCTGACC-3' | 1357 |

FIGURE 3 Nucleotide sequence of cloned copy of SA11 gene 6. The (+) sense strand (corresponding to the mRNA) is shown. The predicted amino acid sequence of the protein product is shown and the termination sites are underlined. Mary K. Estes, et al., Nucleic Acids Research 12(4). 1984.

FIGURE 3A

```
                          MET ASP VAL LEU TYR SER LEU SER LYS THR LEU LYS ASP ALA    14
5'-GGCTTTTAAACGAAGTCTTCAAC ATG GAT GTC CTA TAC TCT TTG TCA AAG ACT CTT AAA GAC GCT   65

ARG ASP LYS ILE VAL GLU GLY THR LEU TYR SER ASN VAL SER ASP LEU ILE GLN GLN PHE    34
     AGA GAC AAA ATT GTC GAA GGC ACA TTG TAT TCT AAC GTG AGT GAT CTA ATT CAA CAA TTT    125

ASN GLN MET ILE ILE THR MET ASN GLY ASN GLU PHE GLN THR GLY GLY ILE GLY ASN LEU    54
     AAT CAA ATG ATA ATT ACT ATG AAT GGA AAT GAA TTT CAA ACT GGA GGA ATC GGT AAT TTG    185

PRO ILE ARG ASN TRP ASN PHE ASN PHE GLY LEU LEU GLY THR THR LEU LEU ASN LEU ASP         74
CCA ATT AGA AAC TGG AAT TTT AAT TTC GGG TTA CTT GGA ACA ACT TTG CTG AAC TTA GAC         245

ALA ASN TYR VAL GLU THR ALA ARG ASN THR ILE ASP TYR PHE VAL ASP PHE VAL ASP ASN         94
GCT AAT TAT GTT GAA ACG GCA AGA AAT ACA ATT GAT TAT TTC GTG GAT TTT GTA GAC AAT         305

VAL CYS MET ASP GLU MET VAL ARG GLU SER GLN ARG ASN GLY ILE ALA PRO GLN SER ASP         114
GTA TGC ATG GAT GAG ATG GTT AGA GAA TCA CAA AGG AAC GGA ATT GCA CCT CAA TCA GAC         365

SER LEU ARG LYS LEU SER ALA ILE LYS PHE LYS AGR ILE ASN PHE ASP ASN SER SER GLU         134
TCG CTA AGA AAG CTG TCA GCC ATT AAA TTC AAA AGA ATA AAT TTT GAT AAT TCG TCG GAA         425

TYR ILE GLU ASN TRP ASN LEU GLN ASN ARG ARG GLN ARG THR GLY PHE THR PHE HIS LYS         154
TAC ATA GAA AAC TGG AAT TTG CAA AAT AGA AGA CAG AGG ACA GGT TTC ACT TTT CAT AAA         485

PRO ASN ILE PHE PRO TYR SER ALA SER PHE THR LEU ASN ARG SER GLN PRO ALA HIS ASP         174
CCA AAC ATT TTT CCT TAT TCA GCA TCA TTT ACA CTA AAT AGA TCA CAA CCC GCT CAT GAT         545

ASN LEU MET GLY THR MET TRP LEU ASN ALA GLY SER GLU ILE GLN VAL ALA GLY PHE ASP         194
AAT TTG ATG GGC ACA ATG TGG TTA AAC GCA GGA TCG GAA ATT CAA GTC GCT GGA TTT GAC         605

TYR SER CYS ALA ILE ASN ALA PRO ALA ASN ILE GLN GLN PHE GLU HIS ILE VAL PRO LEU    214
     TAC TCA TGT GCT ATT AAC GCA CCA GCC AAT ATA CAA CAA TTT GAG CAT ATT GTG CCA CTC    665

ARG ARG VAL LEU THR THR ALA THR ILE THR LEU LEU PRO ASP ALA GLU ARG PHE SER PHE    234
```

```
                CGA AGA GTG TTA ACT ACA GCT ACG ATA ACT CTT CTA CCA GAC GCG GAA AGG TTT AGT TTT           725

PRO ARG VAL ILE ASN SER ALA ASP GLY ALA THR THR TRP PHE PHE ASN PRO VAL ILE LEU                          254
CCA AGA GTG ATC AAT TCA GCT GAC GGG GCA ACT ACA TGG TTT TTC AAC CCA GTG ATT CTC                          785

ARG PRO ASN ASN VAL GLU VAL GLU PHE LEU LEU ASN GLY GLN ILE ILE ASN THR TYR GLN                          274
AGG CCG AAT AAC GTT GAA GTG GAG TTT CTA TTG AAT GGA CAG ATA ATA AAC ACT TAT CAA                          845

ALA ARG PHE GLY THR ILE VAL ALA ARG ASN PHE ASP THR ILE ARG LEU SER PHE GLN LEU                          294
GCA AGA TTT GGA ACT ATC GTA GCT AGA AAT TTT GAT ACT ATT AGA CTA TCA TTC CAG TTA                          905

MET ARG PRO PRO ASN MET THR PRO ALA VAL ALA VAL LEU PHE PRO ASN ALA GLN PRO PHE                          314
ATG AGA CCA CCA AAC ATG ACA CCA GCA GTA GCA GTA CTA TTC CCG AAT GCA CAG CCA TTC                          965

GLU HIS HIS ALA THR VAL GLY LEU THR LEU ARG ILE GLU SER ALA VAL CYS GLU SER VAL                          334
GAA CAT CAT GCA ACA GTG GGA TTG ACA CTT AGA ATT GAG TCT GCA GTT TGT GAG TCT GTA                          1025

LEU ALA ASP ALA SER GLU THR LEU LEU ALA ASN VAL THR SER VAL ARG GLN GLU TYR ALA                          354
CTC GCC GAT GCA AGT GAA ACT CTA TTA GCA AAT GTA ACA TCC GTT AGG CAA GAG TAC GCA                          1085

ILE PRO VAL GLY PRO VAL PHE PRO PRO GLY MET ASN TRP THR ASP LEU ILE THR ASN TYR                          374
ATA CCA GTT GGA CCA GTC TTT CCA CCA GGT ATG AAC TGG ACT GAT TTA ATC ACC AAT TAT                          1145

SER PRO SER ARG GLU ASP ASN LEU GLN ARG VAL PHE THR VAL ALA SER ILE ARG SER MET                          394
TCA CCG TCT AGG GAG GAC AAT TTG CAA CGC GTA TTT ACA GTG GCT TCC ATT AGA AGC ATG                          1205

LEU ILE LYS ⊕⊕⊕                                                                                          397
CTC ATT AAA TGA GGACCAAGCTAACAACTTGGTATCCAACTTTGGTGAGTATGTAGCTATATCAAGCTGTTTGAA                          1280

CTCTGTAAGTAAGGATGCCGTATACGCATTCGCTACACTGAGTTAATCACTCTGATGGTATAGTGAGAGGATCTGACC-3'                        1357
```

FIGURE 3B Nucleotide sequence of cloned copy of SA11 gene 6. The (+) sense strand (corresponding to the mRNA) is shown. The predicted amino acid sequence of the protein product is shown and the termination sites are underlined. Mary K. Estes, et al., Nucleic Acids Research 12(4). 1984.

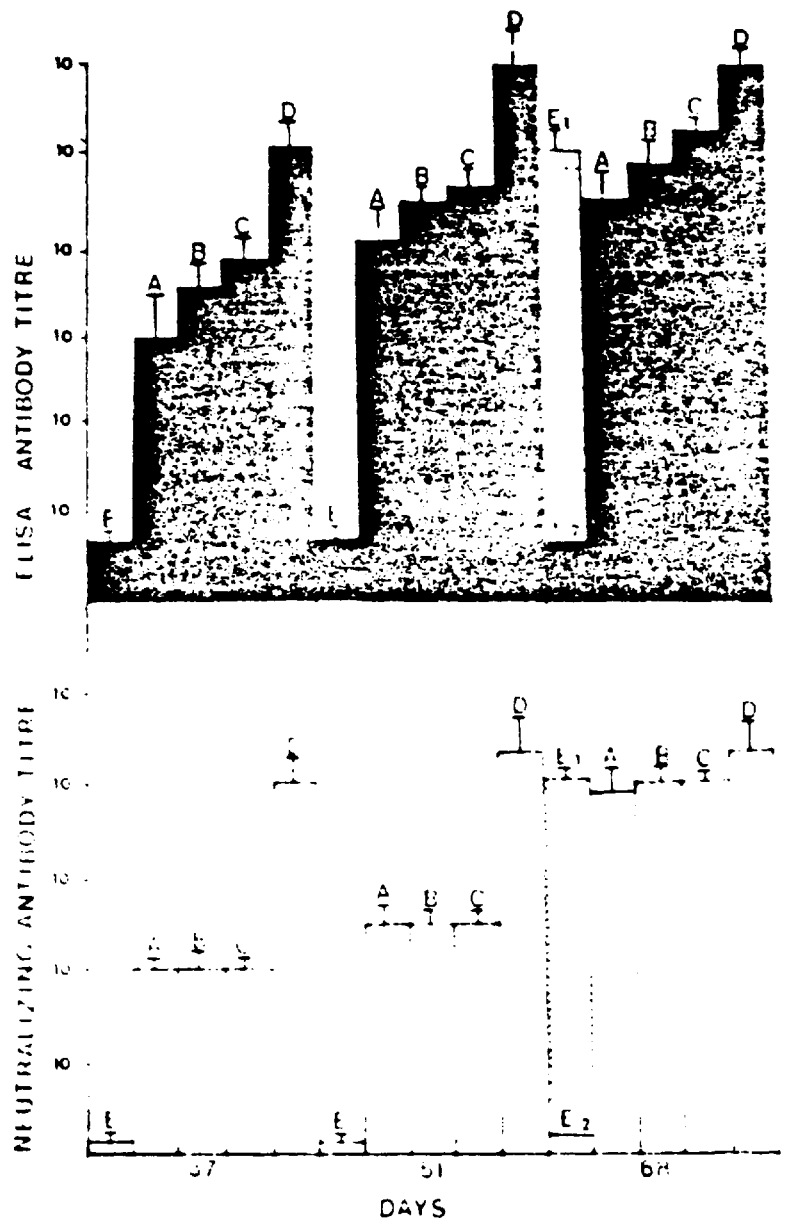

Antibody titers to various preparations of the 14k polypeptide at three different times during the immunization schedule. The upper panel shows total antibody titers as determined by ELISA using double-shelled rotavirus as the antigen. The lower panel shows neutralizing antibody titers as determined by plaque reduction assays. Group A, 14k unconjugated polypeptide; Group B, 14k BSA-conjugated polypeptide; Group C, purified VP7; Group D, infectious bovine rotavirus (BRV); group $E_1$, animals given infectious BRV at 61 days; group $E_2$, animals given for each group is described in more detail in Table 2.

FIGURE 4

ABILITY OF SYNTHETIC PEPTIDES OF VP7 TO BLOCK VIRUS ATTACHMENT TO CELLS. Various amounts of synthetic peptide were adsorbed to $5 \times 10^4$ cells after which time radiolabelled virus was adsorbed to these cells 100% adsorption is equal to $3 \times 10^5$ cpm ● p174-183; ▲ p178-181 ○ p247-259; □ p275-295; ▲ equal amounts of p247-259 and p275-295.

FIGURE 5

VIRUS NEUTRALIZING ANTIBODY TITRES INDUCED IN MICE BY SYNTHETIC PEPTIDES.

Competition of 232-256 VP4 synthetic peptide with the intact 84,000 VP4 for trypsin. Lane A represents the protein profile of double-shelled rotavirus. Lane C-F represents the viral protein profile after incubation of virus for 30 min at 37°C with .0097 ug of trypsin and increasing amounts of synthetic peptide. Lane B represents no synthetic peptide, Lane C has 25 ug; Lane D, 50 ug; Lane E, 75 ug; and Lane F, 200 ug of synthetic peptide. The positioned molecular weight markers are indicated on the left hand side. The arrowheads at Lane B denote the position of the doublet observed at 60,000 and the arrowhead at Lane F denotes the position of the 84,000 protein.

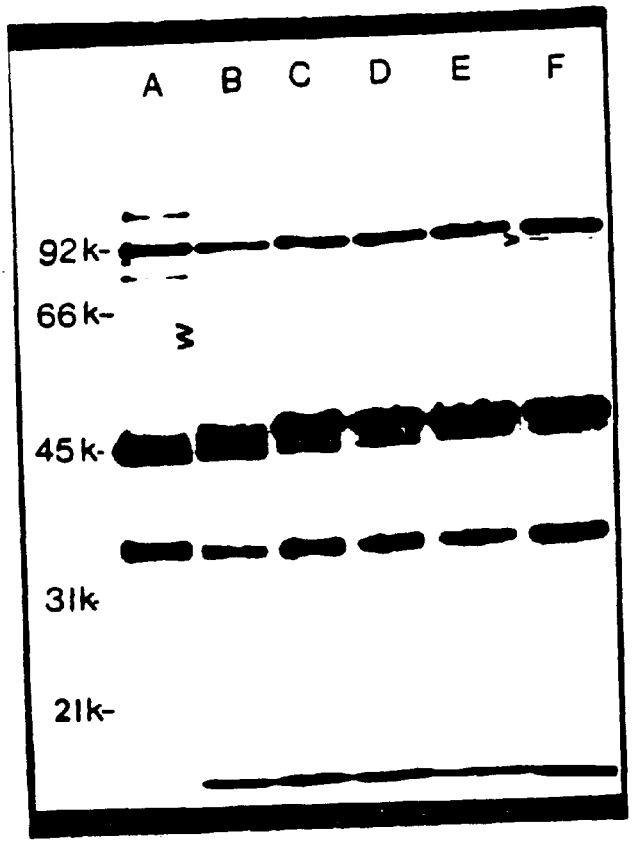

FIGURE 8

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:1:

Tyr Gln Gln Thr Asp Glu Ala Asn Lys
1               5

(2) INFORMATION FOR SEQ ID NO:2:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:2:

Asp Glu Ala Asn Lys Lys Leu Gly Pro Arg Glu Asn Val Ala
1               5                   10

(2) INFORMATION FOR SEQ ID NO:3:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:3:

Arg Asn Cys Lys Lys Leu Gly Pro Arg Glu Asn Val Ala
1               5                   10

(2) INFORMATION FOR SEQ ID NO:4:

(i) SEQUENCE CHARACTERISTICS:
        (A) LENGTH: 21 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:4:

Pro Thr Thr Ala Pro Gln Thr Glu Arg Met Met Arg Ile Asn Trp Lys
1               5                   10                  15

Lys Trp Trp Gln Val
            20

(2) INFORMATION FOR SEQ ID NO:5:

(i) SEQUENCE CHARACTERISTICS:
        (A) LENGTH: 13 amino acids

```
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:5:

Cys Gly Ala Ser Arg Gln Ile Val Tyr Thr Arg Ala Gly
1               5                  10

(2) INFORMATION FOR SEQ ID NO:6:

(i) SEQUENCE CHARACTERISTICS:
            (A) LENGTH: 34 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:6:

Cys Gly Ala Ser Arg Asn Ile Val Tyr Thr Arg Ala Gly Pro Thr Thr
1               5                  10                  15

Ala Pro Gln Thr Glu Arg Met Met Arg Ile Asn Trp Lys Lys Trp Trp
            20                  25                  30

Gln Val (2) INFORMATION FOR SEQ ID NO:7:

(i) SEQUENCE CHARACTERISTICS:
            (A) LENGTH: 25 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:7:

Cys Asn Ile Ala Pro Ala Ser Ile Val Ser Arg Asn Ile Val Tyr Thr
1               5                  10                  15

Arg Ala Gln Pro Asn Gln Asp Ile Ala
            20                  25

(2) INFORMATION FOR SEQ ID NO:8:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:8:

Cys Gly Ala Ser Arg Asn Ile Val Tyr Thr Arg Ala
1               5                  10

(2) INFORMATION FOR SEQ ID NO:9:

(i) SEQUENCE CHARACTERISTICS:
            (A) LENGTH: 23 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:9:
```

```
Thr Met Asn Gly Asn Glu Phe Gln Thr Gly Gly Ile Gly Asn Leu Pro
1               5                   10                  15

Ile Arg Asn Trp Asn Gly Cys
                20
```

(2) INFORMATION FOR SEQ ID NO:10:

(i) SEQUENCE CHARACTERISTICS:
        (A) LENGTH: 25 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:10:

```
Cys Asn Ile Val Pro Val Ser Ile Val Ser Arg Asn Ile Ala Tyr Thr
1               5                   10                  15

Arg Ala Gln Pro Asn Gln Asp Ile Ala
                20                  25
```

(2) INFORMATION FOR SEQ ID NO:11:

(i) SEQUENCE CHARACTERISTICS:
        (A) LENGTH: 326 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:11:

```
Met Tyr Gly Ile Glu Tyr Thr Thr Ile Leu Thr Ile Leu Ile Ser Ile
1               5                   10                  15

Ile Leu Leu Asn Tyr Ile Leu Lys Thr Ile Thr Asn Thr Met Asp Tyr
                20                  25                  30

Ile Ile Phe Arg Phe Leu Leu Leu Ile Ala Leu Ile Ser Pro Phe Val
            35                  40                  45

Arg Thr Gln Asn Tyr Gly Met Tyr Leu Pro Ile Thr Gly Ser Leu Asp
        50                  55                  60

Ala Val Tyr Thr Asn Ser Thr Ser Gly Glu Pro Phe Leu Thr Ser Thr
65                  70                  75                  80

Leu Cys Leu Tyr Tyr Pro Ala Glu Ala Lys Asn Glu Ile Ser Asp Asp
                85                  90                  95

Glu Trp Glu Asn Thr Leu Ser Gln Leu Phe Leu Thr Lys Gly Trp Pro
                100                 105                 110

Ile Gly Ser Val Tyr Phe Lys Asp Tyr Asn Asp Ile Asn Thr Phe Ser
            115                 120                 125

Val Asn Pro Gln Leu Tyr Cys Asp Tyr Asn Val Val Leu Met Arg Tyr
        130                 135                 140

Asp Asn Thr Ser Glu Leu Asp Ala Ser Glu Leu Ala Asp Leu Ile Leu
145                 150                 155                 160

Asn Glu Trp Leu Cys Asn Pro Met Asp Ile Ser Leu Tyr Tyr Tyr Gln
                165                 170                 175

Gln Ser Ser Glu Ser Asn Lys Trp Ile Ser Met Gly Thr Asp Cys Thr
                180                 185                 190

Val Lys Val Cys Pro Leu Asn Thr Gln Thr Leu Gly Ile Gly Cys Lys
            195                 200                 205

Thr Thr Asp Val Asn Thr Phe Glu Ile Val Ala Ser Ser Glu Lys Leu
```

-continued

```
                210                 215                 220
Val Ile Thr Asp Val Val Asn Gly Val Asn His Asn Ile Asn Ile Ser
225                 230                 235                 240

Ile Asn Thr Cys Thr Ile Arg Asn Cys Asn Lys Leu Gly Pro Arg Glu
                245                 250                 255

Asn Val Ala Ile Ile Gln Val Gly Pro Asn Ala Leu Asp Ile Thr
                260                 265                 270

Ala Asp Pro Thr Thr Val Pro Gln Val Gln Arg Ile Met Arg Ile Asn
                275                 280                 285

Trp Lys Lys Trp Trp Gln Val Phe Tyr Thr Val Val Asp Tyr Ile Asn
290                 295                 300

Gln Val Ile Gln Val Met Ser Lys Arg Ser Arg Ser Leu Asp Ala Ala
305                 310                 315                 320

Ala Phe Tyr Tyr Arg Ile
                325
```

(2) INFORMATION FOR SEQ ID NO:12:

(i) SEQUENCE CHARACTERISTICS:
        (A) LENGTH: 326 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:12:

```
Met Tyr Gly Ile Glu Tyr Thr Thr Val Leu Thr Phe Leu Ile Ser Thr
1               5                   10                  15

Ile Leu Leu Asn Tyr Ile Leu Lys Ser Leu Thr Arg Ile Met Asp Phe
                20                  25                  30

Ile Ile Tyr Arg Phe Leu Phe Ile Ile Val Ile Leu Ser Pro Phe Leu
                35                  40                  45

Arg Ala Gln Asn Tyr Gly Ile Asn Leu Pro Ile Ala Gly Ser Met Asp
                50                  55                  60

Thr Ala Tyr Ala Asn Ser Thr Gln Glu Glu Pro Phe Leu Thr Ser Thr
65                  70                  75                  80

Leu Cys Leu Tyr Tyr Pro Thr Glu Ala Ala Thr Glu Ile Asn Asp Asn
                85                  90                  95

Ser Trp Lys Asp Thr Leu Ser Gln Leu Phe Leu Thr Lys Gly Trp Pro
                100                 105                 110

Thr Glu Ser Val Tyr Phe Lys Glu Tyr Thr Asn Ile Ala Ser Phe Ser
                115                 120                 125

Val Asp Pro Gln Leu Tyr Cys Asp Tyr Asn Val Val Leu Met Lys Tyr
                130                 135                 140

Asp Ala Thr Leu Gln Leu Asp Met Ser Glu Leu Ala Asp Leu Ile Leu
145                 150                 155                 160

Asn Glu Trp Leu Cys Asn Pro Met Asp Ile Thr Leu Tyr Tyr Gln
                165                 170                 175

Gln Thr Asp Glu Ala Asn Lys Trp Ile Ser Met Gly Ser Ser Cys Thr
                180                 185                 190

Ile Lys Val Cys Pro Leu Asn Thr Gln Thr Leu Gly Ile Gly Cys Leu
                195                 200                 205

Thr Thr Asp Ala Thr Thr Phe Glu Glu Val Pro Thr Ala Glu Lys Leu
                210                 215                 220

Val Ile Thr Asp Val Val Asp Gly Val Asn His Lys Leu Asp Val Thr
```

```
225                 230                 235                 240

Thr Ala Thr Cys Thr Ile Arg Asn Cys Lys Lys Leu Gly Pro Arg Glu
                245                 250                 255

Asn Val Ala Val Ile Gln Val Gly Gly Ser Asp Ile Leu Asp Ile Thr
                260                 265                 270

Ala Asp Pro Thr Thr Ala Pro Gln Thr Glu Arg Met Met Arg Ile Asn
            275                 280                 285

Trp Lys Lys Trp Trp Gln Val Phe Tyr Thr Val Val Asp Tyr Val Asp
        290                 295                 300

Gln Ile Ile Gln Val Met Ser Lys Arg Ser Arg Ser Leu Asn Ser Ala
305                 310                 315                 320

Ala Phe Tyr Tyr Arg Val
                325

(2) INFORMATION FOR SEQ ID NO:13:

(i) SEQUENCE CHARACTERISTICS:
        (A) LENGTH: 326 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:13:

Met Tyr Gly Ile Glu Tyr Thr Thr Ile Leu Ile Phe Leu Thr Ser Ile
1                5                  10                  15

Thr Leu Leu Asn Tyr Ile Leu Lys Ser Ile Thr Arg Ile Met Asp Tyr
                20                  25                  30

Ile Ile Tyr Arg Phe Leu Leu Ile Val Val Val Leu Ala Thr Met Ile
            35                  40                  45

Arg Ala Gln Asn Tyr Gly Val Asn Leu Pro Ile Thr Gly Ser Met Asp
        50                  55                  60

Thr Ala Tyr Ala Asp Ser Thr Gln Ser Glu Pro Phe Leu Thr Ser Thr
65                  70                  75                  80

Leu Cys Leu Tyr Tyr Pro Val Glu Ala Ser Asn Glu Ile Ala Asp Thr
                85                  90                  95

Glu Trp Lys Asp Thr Leu Ser Gln Leu Phe Leu Thr Lys Gly Trp Pro
                100                 105                 110

Thr Gly Ser Val Tyr Leu Lys Glu Tyr Ala Asp Ile Ala Ala Phe Ser
            115                 120                 125

Val Glu Pro Gln Leu Tyr Cys Asp Tyr Asn Leu Val Leu Met Lys Tyr
        130                 135                 140

Asp Ser Thr Gln Glu Leu Asp Met Ser Glu Leu Ala Asp Leu Ile Leu
145                 150                 155                 160

Asn Glu Trp Leu Cys Asn Pro Met Asp Ile Thr Leu Tyr Tyr Tyr Gln
                165                 170                 175

Gln Thr Asp Glu Ala Asn Lys Trp Ile Ser Thr Gly Ser Ser Cys Thr
                180                 185                 190

Val Lys Val Cys Pro Leu Asn Thr Gln Thr Leu Gly Ile Gly Cys Leu
            195                 200                 205

Ile Thr Asn Pro Asp Thr Phe Glu Thr Val Ala Thr Met Glu Lys Leu
        210                 215                 220

Val Ile Thr Asp Val Val Asp Gly Val Asn His Lys Leu Asn Val Thr
225                 230                 235                 240

Thr Ala Thr Cys Thr Ile Arg Asn Cys Lys Lys Leu Gly Pro Arg Glu
```

```
               245                 250                 255
Asn Val Ala Val Ile Gln Val Gly Gly Ala Asn Val Leu Asp Ile Thr
                260                 265                 270

Ala Asp Pro Thr Thr Ala Pro Gln Thr Glu Arg Met Met Arg Ile Asn
            275                 280                 285

Trp Lys Lys Trp Trp Gln Val Phe Tyr Thr Val Val Asp Tyr Val Asn
        290                 295                 300

Gln Ile Ile Gln Thr Met Ser Lys Arg Ser Arg Ser Leu Asn Ser Ser
305                 310                 315                 320

Ala Phe Tyr Tyr Arg Val
                325
```

(2) INFORMATION FOR SEQ ID NO:14:

(i) SEQUENCE CHARACTERISTICS:
        (A) LENGTH: 326 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:14:

```
Met Tyr Gly Ile Glu Tyr Thr Thr Ile Leu Ile Phe Leu Thr Ser Ile
1               5                   10                  15

Thr Leu Leu Asn Tyr Ile Leu Lys Ser Ile Thr Arg Met Met Asp Tyr
            20                  25                  30

Ile Ile Tyr Arg Phe Leu Leu Ile Val Val Ile Leu Ala Thr Ile Ile
        35                  40                  45

Asn Ala Gln Asn Tyr Gly Val Asn Leu Pro Ile Thr Gly Ser Met Asp
    50                  55                  60

Thr Ala Tyr Ala Asp Ser Thr Gln Ser Glu Pro Phe Leu Thr Ser Thr
65                  70                  75                  80

Leu Cys Leu Tyr Tyr Pro Val Glu Ala Ser Asn Glu Ile Ala Asp Thr
                85                  90                  95

Glu Trp Lys Asp Thr Leu Ser Gln Leu Phe Leu Thr Lys Gly Trp Pro
            100                 105                 110

Thr Gly Ser Val Tyr Leu Lys Glu Tyr Ala Asp Ile Ala Ala Phe Ser
        115                 120                 125

Val Glu Pro Gln Leu Tyr Cys Asp Tyr Asn Leu Val Leu Met Lys Tyr
    130                 135                 140

Asp Ser Thr Gln Glu Leu Asp Met Ser Glu Leu Ala Asp Leu Ile Leu
145                 150                 155                 160

Asn Glu Trp Leu Cys Asn Pro Met Asp Ile Thr Leu Tyr Tyr Tyr Gln
                165                 170                 175

Gln Thr Asp Glu Ala Asn Lys Trp Ile Ser Thr Gly Ser Ser Cys Thr
            180                 185                 190

Val Lys Val Cys Pro Leu Asn Thr Gln Thr Leu Gly Ile Gly Cys Leu
        195                 200                 205

Ile Thr Asn Pro Asp Thr Phe Glu Thr Val Ala Thr Met Glu Lys Leu
    210                 215                 220

Val Ile Thr Asp Val Val Asp Gly Val Asn His Lys Leu Asn Val Thr
225                 230                 235                 240

Thr Ala Thr Cys Thr Ile Arg Asn Cys Lys Lys Leu Gly Pro Arg Glu
                245                 250                 255

Asn Val Ala Val Ile Gln Val Gly Gly Ala Asn Val Leu Asp Ile Thr
```

-continued

```
                260                 265                 270
Ala Asp Pro Thr Thr Pro Gln Thr Glu Arg Met Met Arg Ile Asn
            275                 280                 285

Trp Lys Lys Trp Trp Gln Val Phe Tyr Thr Val Val Asp Tyr Val Asn
290                 295                 300

Gln Ile Ile Gln Thr Met Ser Lys Arg Ser Arg Ser Leu Asn Ser Ser
305                 310                 315                 320

Ala Phe Tyr Tyr Arg Val
                325

(2) INFORMATION FOR SEQ ID NO:15:

(i) SEQUENCE CHARACTERISTICS:
        (A) LENGTH: 776 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:15:

Met Ala Ser Leu Ile Tyr Arg Gln Leu Leu Thr Asn Ser Tyr Thr Val
1               5                   10                  15

Glu Leu Ser Asp Glu Ile Gln Glu Ile Gly Ser Thr Lys Thr Gln Asn
                20                  25                  30

Val Thr Val Asn Pro Gly Pro Phe Ala Gln Thr Asn Tyr Ala Ser Val
            35                  40                  45

Asn Trp Gly Pro Gly Glu Thr Asn Asp Ser Thr Thr Val Glu Pro Val
    50                  55                  60

Leu Asp Gly Pro Tyr Gln Pro Thr Thr Phe Asn Pro Pro Val Ser Tyr
65                  70                  75                  80

Trp Met Leu Leu Ala Pro Thr Asn Ala Gly Val Val Asp Gln Gly Thr
                85                  90                  95

Asn Asn Thr Asn Arg Trp Leu Ala Thr Ile Leu Ile Lys Pro Asn Val
                100                 105                 110

Gln Gln Val Glu Arg Thr Tyr Thr Leu Phe Gly Gln Gln Val Gln Val
            115                 120                 125

Thr Val Ser Asn Asp Ser Gln Thr Lys Trp Lys Phe Val Asp Leu Ser
    130                 135                 140

Lys Gln Thr Gln Asp Gly Asn Tyr Ser Gln His Gly Pro Leu Leu Ser
145                 150                 155                 160

Thr Pro Lys Leu Tyr Gly Val Met Lys His Gly Gly Lys Ile Tyr Thr
                165                 170                 175

Tyr Asn Gly Glu Thr Pro Asn Ala Thr Thr Gly Tyr Tyr Ser Thr Thr
                180                 185                 190

Asn Phe Asp Thr Val Asn Met Thr Ala Tyr Cys Asp Phe Tyr Ile Ile
            195                 200                 205

Pro Leu Ala Gln Glu Ala Lys Cys Thr Glu Tyr Ile Asn Asn Gly Leu
    210                 215                 220

Pro Pro Ile Gln Asn Thr Arg Asn Ile Val Pro Val Ser Ile Val Ser
225                 230                 235                 240

Arg Asn Ile Val Tyr Thr Arg Ala Gln Pro Asn Gln Asp Ile Val Val
                245                 250                 255

Ser Lys Thr Ser Leu Trp Lys Glu Met Gln Tyr Asn Arg Asp Ile Val
                260                 265                 270

Ile Arg Phe Lys Phe Ala Asn Ser Ile Ile Lys Ser Gly Gly Leu Gly
```

```
            275                 280                 285
Tyr Lys Trp Ser Glu Val Ser Phe Lys Pro Ala Asn Tyr Gln Tyr Thr
        290                 295                 300
Tyr Thr Arg Asp Gly Glu Val Thr Ala His Thr Thr Cys Ser Val
305                 310                 315                 320
Asn Gly Ile Asn Asp Phe Asn Tyr Asn Gly Gly Ser Leu Pro Thr Asp
                325                 330                 335
Phe Val Ile Ser Lys Tyr Glu Val Ile Lys Glu Asn Ser Phe Val Tyr
                340                 345                 350
Ile Asp Tyr Trp Asp Asp Ser Gln Ala Phe Arg Asn Met Val Tyr Val
                355                 360                 365
Arg Ser Leu Ala Ala Asp Leu Asn Ser Val Met Cys Thr Gly Gly Asp
370                 375                 380
Tyr Ser Phe Ala Ile Pro Val Gly Asn Tyr Pro Val Met Thr Gly Gly
385                 390                 395                 400
Ala Val Ser Leu His Ser Ala Gly Val Thr Leu Ser Thr Gln Phe Thr
                405                 410                 415
Asp Phe Val Ser Leu Asn Ser Leu Arg Phe Arg Phe Arg Leu Ser Val
                420                 425                 430
Glu Glu Pro Pro Phe Ser Ile Leu Arg Thr Arg Val Ser Gly Leu Tyr
                435                 440                 445
Gly Leu Pro Ala Ala Lys Pro Asn Asn Ser Gln Glu Tyr Tyr Glu Ile
450                 455                 460
Ala Gly Arg Phe Ser Leu Ile Ser Leu Val Pro Ser Asn Asp Asp Tyr
465                 470                 475                 480
Gln Thr Pro Ile Ile Asn Ser Val Thr Val Arg Gln Asp Leu Glu Arg
                485                 490                 495
Gln Leu Gly Glu Leu Arg Asp Glu Phe Asn Asn Leu Ser Gln Gln Ile
                500                 505                 510
Ala Met Ser Gln Leu Ile Asp Leu Ala Leu Leu Pro Leu Asp Met Phe
                515                 520                 525
Ser Met Phe Ser Gly Ile Lys Ser Thr Ile Asp Ala Ala Lys Ser Met
                530                 535                 540
Ala Thr Asn Val Met Lys Arg Phe Lys Lys Ser Ser Leu Ala Asn Ser
545                 550                 555                 560
Val Ser Thr Leu Thr Asp Ser Leu Ser Asp Ala Ala Ser Ser Ile Ser
                565                 570                 575
Arg Ser Ala Ser Val Arg Ser Val Ser Ser Thr Ala Ser Ala Trp Thr
                580                 585                 590
Glu Val Ser Asn Ile Thr Ser Asp Ile Asn Val Thr Thr Ser Ser Ile
                595                 600                 605
Ser Thr Gln Thr Ser Thr Ile Ser Arg Arg Leu Arg Leu Lys Glu Met
        610                 615                 620
Ala Thr Gln Thr Asp Gly Met Asn Phe Asp Asp Ile Ser Ala Ala Val
625                 630                 635                 640
Leu Lys Thr Lys Ile Asp Lys Ser Thr Gln Leu Asn Thr Asn Thr Leu
                645                 650                 655
Pro Glu Ile Val Thr Glu Ala Ser Glu Lys Phe Ile Pro Asn Arg Ala
                660                 665                 670
Tyr Arg Val Ile Lys Asp Asp Glu Val Leu Glu Ala Ser Thr Asp Gly
                675                 680                 685
Lys Tyr Phe Ala Tyr Lys Val Glu Thr Ile Leu Lys Arg Phe His Ser
        690                 695                 700
```

```
Met Tyr Lys Phe Ala Asp Leu Val Thr Asp Ser Pro Val Ile Ser Ala
705                 710                 715                 720

Ile Ile Asp Phe Lys Thr Leu Lys Asn Leu Asn Asp Asn Tyr Gly Ile
            725                 730                 735

Ser Arg Gln Gln Ala Leu Asn Leu Leu Arg Ser Asp Pro Arg Val Leu
                740                 745                 750

Arg Glu Phe Ile Asn Gln Asp Asn Pro Ile Ile Arg Asn Arg Ile Glu
            755                 760                 765

Ser Leu Ile Met Gln Cys Arg Leu
        770                 775

(2) INFORMATION FOR SEQ ID NO:16:

(i) SEQUENCE CHARACTERISTICS:
        (A) LENGTH: 747 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:16:

Leu Ile Tyr Arg Gln Leu Leu Thr Asn Ser Tyr Thr Val Glu Leu Ser
1               5                   10                  15

Asp Glu Ile Gln Glu Ile Gly Ser Thr Lys Thr Gln Asn Val Thr Val
            20                  25                  30

Asn Pro Gly Pro Phe Ala Gln Thr Asn Tyr Ala Pro Val Asn Trp Gly
            35                  40                  45

Pro Gly Glu Thr Asn Asp Ser Thr Thr Val Glu Pro Val Leu Asp Gly
50                  55                  60

Pro Tyr Gln Pro Thr Thr Phe Asn Pro Pro Val Ser Tyr Trp Met Leu
65                  70                  75                  80

Leu Ala Pro Thr Asn Ala Gly Val Val Glu Gly Thr Asn Asn Thr
                85                  90                  95

Asn Arg Trp Leu Ala Thr Ile Leu Ile Glu Pro Asn Val Gln Gln Val
            100                 105                 110

Glu Arg Thr Tyr Thr Leu Phe Gly Gln Gln Val Gln Val Thr Val Ser
            115                 120                 125

Asn Asp Ser Gln Thr Lys Trp Lys Phe Val Asp Leu Ser Lys Gln Thr
130                 135                 140

Gln Asp Gly Asn Tyr Ser Gln His Gly Ser Leu Leu Ser Thr Pro Lys
145                 150                 155                 160

Leu Tyr Gly Val Met Lys His Gly Gly Lys Ile Tyr Thr Tyr Asn Gly
                165                 170                 175

Glu Thr Pro Asn Ala Asn Thr Gly Tyr Tyr Ser Thr Thr Asn Phe Asp
            180                 185                 190

Thr Val Asn Met Thr Ala Tyr Cys Asp Phe Tyr Ile Ile Pro Leu Ala
            195                 200                 205

Gln Glu Ala Lys Cys Thr Glu Tyr Ile Asn Asn Gly Leu Pro Pro Ile
            210                 215                 220

Gln Asn Thr Arg Asn Ile Val Pro Val Ser Ile Val Ser Arg Asn Ile
225                 230                 235                 240

Val Tyr Thr Arg Ala Gln Pro Asn Gln Asp Ile Val Val Ser Lys Thr
                245                 250                 255

Ser Leu Trp Lys Glu Met Gln Tyr Asn Arg Asp Ile Val Ile Arg Phe
            260                 265                 270
```

-continued

```
Lys Phe Ala Asn Ser Ile Ile Lys Ser Gly Leu Gly Tyr Lys Trp
            275                 280                 285
Ser Glu Val Ser Phe Lys Pro Ala Phe Tyr Gln Tyr Thr Tyr Thr Arg
290                 295                 300
Asp Gly Glu Glu Val Thr Ala His Thr Thr Cys Ser Val Asn Gly Val
305                 310                 315                 320
Asn Asp Phe Asn Tyr Asn Gly Gly Ser Leu Pro Thr Asp Phe Val Ile
                325                 330                 335
Ser Lys Tyr Glu Val Ile Lys Glu Asn Ser Phe Val Tyr Ile Asp Tyr
            340                 345                 350
Trp Asp Asp Ser Gln Ala Phe Arg Asn Met Val Tyr Val Arg Ser Leu
            355                 360                 365
Ala Ala Asp Leu Asn Ser Val Met Cys Thr Gly Gly Asp Tyr Ser Phe
370                 375                 380
Ala Leu Pro Val Gly Asn Tyr Pro Val Met Thr Gly Gly Ala Val Ser
385                 390                 395                 400
Leu His Ser Ala Gly Val Thr Leu Ser Thr Gln Phe Thr Asp Phe Val
                405                 410                 415
Ser Leu Asn Ser Leu Arg Phe Arg Phe Arg Leu Ser Val Glu Glu Pro
            420                 425                 430
Pro Phe Ser Ile Leu Arg Thr Arg Val Ser Gly Leu Tyr Gly Leu Pro
            435                 440                 445
Ala Ala Lys Pro Asn Asn Ser Gln Glu Tyr Tyr Glu Ile Ala Gly Arg
            450                 455                 460
Phe Ser Leu Ile Ser Leu Val Pro Leu Asn Asp Asp Tyr Gln Thr Pro
465                 470                 475                 480
Ile Met Asn Ser Val Thr Val Arg Gln Asp Leu Glu Arg Gln Leu Gly
                485                 490                 495
Glu Leu Arg Asp Glu Phe Asn Asn Leu Ser Gln Gln Ile Ala Met Ser
                500                 505                 510
Gln Leu Ile Asp Leu Ala Leu Leu Pro Leu Asp Met Phe Ser Met Phe
            515                 520                 525
Ser Gly Ile Lys Ser Thr Ile Asp Ala Ala Lys Ser Met Ala Thr Asn
            530                 535                 540
Val Met Lys Arg Phe Lys Lys Ser Ser Leu Ala Asn Ser Val Ser Thr
545                 550                 555                 560
Leu Thr Asp Ser Leu Ser Asp Ala Ala Ser Ser Ile Ser Arg Ser Ala
                565                 570                 575
Ser Val Arg Ser Val Ser Ser Thr Ala Ser Ala Trp Thr Glu Val Ser
            580                 585                 590
Asn Ile Ala Ser Asp Ile Asn Val Thr Thr Ser Ser Ile Ser Thr Gln
            595                 600                 605
Thr Ser Thr Ile Ser Arg Arg Leu Arg Leu Lys Glu Met Ala Thr Gln
            610                 615                 620
Thr Asp Gly Met Asn Phe Asp Asp Ile Ser Ala Ala Val Leu Lys Thr
625                 630                 635                 640
Lys Ile Asp Lys Ser Thr Gln Leu Asn Thr Asn Thr Leu Pro Glu Ile
                645                 650                 655
Val Thr Glu Ala Ser Glu Lys Phe Ile Pro Asn Arg Ala Tyr Arg Val
            660                 665                 670
Ile Lys Asp Asp Glu Val Leu Glu Ala Ser Ile Asp Gly Lys Tyr Phe
            675                 680                 685
```

```
Ala Tyr Lys Val Glu Thr Phe Glu Ile Pro Phe Asp Val Gln Lys
    690             695                 700

Phe Ala Asp Leu Val Thr Asp Ser Pro Val Ile Ser Ala Ile Asp
705             710                 715                 720

Phe Lys Thr Leu Lys Asn Leu Asn Asp Asn Tyr Gly Ile Ser Arg Gln
                725                 730                 735

Gln Ala Leu Asn Leu Leu Arg Ser Asp Pro Arg
        740                 745
```

(2) INFORMATION FOR SEQ ID NO:17:

(i) SEQUENCE CHARACTERISTICS:
        (A) LENGTH: 1357 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 24..1214

(xi) SEQUENCE DESCRIPTION: SEQ ID NO:17:

```
GGCTTTTAAA CGAAGTCTTC AAC ATG GAT GTC CTA TAC TCT TTG TCA AAG          50
                         Met Asp Val Leu Tyr Ser Leu Ser Lys
                           1               5

ACT CTT AAA GAC GCT AGA GAC AAA ATT GTC GAA GGC ACA TTG TAT TCT        98
Thr Leu Lys Asp Ala Arg Asp Lys Ile Val Glu Gly Thr Leu Tyr Ser
 10              15                  20                  25

AAC GTG AGT GAT CTA ATT CAA CAA TTT AAT CAA ATG ATA ATT ACT ATG       146
Asn Val Ser Asp Leu Ile Gln Gln Phe Asn Gln Met Ile Ile Thr Met
             30                  35                  40

AAT GGA AAT GAA TTT CAA ACT GGA GGA ATC GGT AAT TTG CCA ATT AGA       194
Asn Gly Asn Glu Phe Gln Thr Gly Gly Ile Gly Asn Leu Pro Ile Arg
                 45                  50                  55

AAC TGG AAT TTT AAT TTC GGG TTA CTT GGA ACA ACT TTG CTG AAC TTA       242
Asn Trp Asn Phe Asn Phe Gly Leu Leu Gly Thr Thr Leu Leu Asn Leu
             60                  65                  70

GAC GCT AAT TAT GTT GAA ACG GCA AGA AAT ACA ATT GAT TAT TTC GTG       290
Asp Ala Asn Tyr Val Glu Thr Ala Arg Asn Thr Ile Asp Tyr Phe Val
 75                  80                  85

GAT TTT GTA GAC AAT GTA TGC ATG GAT GAG ATG GTT AGA GAA TCA CAA       338
Asp Phe Val Asp Asn Val Cys Met Asp Glu Met Val Arg Glu Ser Gln
 90                  95                 100                 105

AGG AAC GGA ATT GCA CCT CAA TCA GAC TCG CTA AGA AAG CTG TCA GCC       386
Arg Asn Gly Ile Ala Pro Gln Ser Asp Ser Leu Arg Lys Leu Ser Ala
             110                 115                 120

ATT AAA TTC AAA AGA ATA AAT TTT GAT AAT TCG TCG GAA TAC ATA GAA       434
Ile Lys Phe Lys Arg Ile Asn Phe Asp Asn Ser Ser Glu Tyr Ile Glu
             125                 130                 135

AAC TGG AAT TTG CAA AAT AGA AGA CAG AGG ACA GGT TTC ACT TTT CAT       482
Asn Trp Asn Leu Gln Asn Arg Arg Gln Arg Thr Gly Phe Thr Phe His
             140                 145                 150

AAA CCA AAC ATT TTT CCT TAT TCA GCA TCA TTT ACA CTA AAT AGA TCA       530
Lys Pro Asn Ile Phe Pro Tyr Ser Ala Ser Phe Thr Leu Asn Arg Ser
 155                 160                 165

CAA CCC GCT CAT GAT AAT TTG ATG GGC ACA ATG TGG TTA AAC GCA GGA       578
Gln Pro Ala His Asp Asn Leu Met Gly Thr Met Trp Leu Asn Ala Gly
 170                 175                 180                 185

TCG GAA ATT CAA GTC GCT GGA TTT GAC TAC TCA TGT GCT ATT AAC GCA       626
Ser Glu Ile Gln Val Ala Gly Phe Asp Tyr Ser Cys Ala Ile Asn Ala
```

```
                    190                 195                 200
CCA GCC AAT ATA CAA CAA TTT GAG CAT ATT GTG CCA CTC CGA AGA GTG      674
Pro Ala Asn Ile Gln Gln Phe Glu His Ile Val Pro Leu Arg Arg Val
            205                 210                 215

TTA ACT ACA GCT ACG ATA ACT CTT CTA CCA GAC GCG GAA AGG TTT AGT      722
Leu Thr Thr Ala Thr Ile Thr Leu Leu Pro Asp Ala Glu Arg Phe Ser
            220                 225                 230

TTT CCA AGA GTG ATC AAT TCA GCT GAC GGG GCA ACT ACA TGG TTT TTC      770
Phe Pro Arg Val Ile Asn Ser Ala Asp Gly Ala Thr Thr Trp Phe Phe
            235                 240                 245

AAC CCA GTG ATT CTC AGG CCG AAT AAC GTT GAA GTG GAG TTT CTA TTG      818
Asn Pro Val Ile Leu Arg Pro Asn Asn Val Glu Val Glu Phe Leu Leu
250                 255                 260                 265

AAT GGA CAG ATA ATA AAC ACT TAT CAA GCA AGA TTT GGA ACT ATC GTA      866
Asn Gly Gln Ile Ile Asn Thr Tyr Gln Ala Arg Phe Gly Thr Ile Val
            270                 275                 280

GCT AGA AAT TTT GAT ACT ATT AGA CTA TCA TTC CAG TTA ATG AGA CCA      914
Ala Arg Asn Phe Asp Thr Ile Arg Leu Ser Phe Gln Leu Met Arg Pro
            285                 290                 295

CCA AAC ATG ACA CCA GCA GTA GCA GTA CTA TTC CCG AAT GCA CAG CCA      962
Pro Asn Met Thr Pro Ala Val Ala Val Leu Phe Pro Asn Ala Gln Pro
            300                 305                 310

TTC GAA CAT CAT GCA ACA GTG GGA TTG ACA CTT AGA ATT GAG TCT GCA     1010
Phe Glu His His Ala Thr Val Gly Leu Thr Leu Arg Ile Glu Ser Ala
            315                 320                 325

GTT TGT GAG TCT GTA CTC GCC GAT GCA AGT GAA ACT CTA TTA GCA AAT     1058
Val Cys Glu Ser Val Leu Ala Asp Ala Ser Glu Thr Leu Leu Ala Asn
330                 335                 340                 345

GTA ACA TCC GTT AGG CAA GAG TAC GCA ATA CCA GTT GGA CCA GTC TTT     1106
Val Thr Ser Val Arg Gln Glu Tyr Ala Ile Pro Val Gly Pro Val Phe
            350                 355                 360

CCA CCA GGT ATG AAC TGG ACT GAT TTA ATC ACC AAT TAT TCA CCG TCT     1154
Pro Pro Gly Met Asn Trp Thr Asp Leu Ile Thr Asn Tyr Ser Pro Ser
            365                 370                 375

AGG GAG GAC AAT TTG CAA CGC GTA TTT ACA GTG GCT TCC ATT AGA AGC     1202
Arg Glu Asp Asn Leu Gln Arg Val Phe Thr Val Ala Ser Ile Arg Ser
            380                 385                 390

ATG CTC ATT AAA TGAGGACCAA GCTAACAACT TGGTATCCAA CTTTGGTGAG         1254
Met Leu Ile Lys
            395

TATGTAGCTA TATCAAGCTG TTTGAACTCT GTAAGTAAGG ATGCGTATAC GCATTCGCTA   1314

CACTGAGTTA ATCACTCTGA TGGTATAGTG AGAGGATGTG ACC                     1357

(2) INFORMATION FOR SEQ ID NO:18:

(i) SEQUENCE CHARACTERISTICS:
        (A) LENGTH: 397 amino acids
        (B) TYPE: amino acid
        (D) TOPOLOGY: linear (ii) MOLECULE TYPE: protein (xi) SEQUENCE DESCRIPTION: SEQ ID NO:18:

Met Asp Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Ile Ile Thr Met Asn Gly Asn Glu Phe Gln Thr
            35                  40                  45
```

Gly Gly Ile Gly Asn Leu Pro Ile Arg Asn Trp Asn Phe Asn Phe Gly
            50                  55                  60

Leu Leu Gly Thr Thr Leu Leu Asn Leu Asp Ala Asn Tyr Val Glu Thr
65                  70                  75                  80

Ala Arg Asn Thr Ile Asp Tyr Phe Val Asp Phe Val Asp Asn Val Cys
                        85                  90                  95

Met Asp Glu Met Val Arg Glu Ser Gln Arg Asn Gly Ile Ala Pro Gln
                100                 105                 110

Ser Asp Ser Leu Arg Lys Leu Ser Ala Ile Lys Phe Lys Arg Ile Asn
            115                 120                 125

Phe Asp Asn Ser Ser Glu Tyr Ile Glu Asn Trp Asn Leu Gln Asn Arg
        130                 135                 140

Arg Gln Arg Thr Gly Phe Thr Phe His Lys Pro Asn Ile Phe Pro Tyr
145                 150                 155                 160

Ser Ala Ser Phe Thr Leu Asn Arg Ser Gln Pro Ala His Asp Asn Leu
                        165                 170                 175

Met Gly Thr Met Trp Leu Asn Ala Gly Ser Glu Ile Gln Val Ala Gly
                180                 185                 190

Phe Asp Tyr Ser Cys Ala Ile Asn Ala Pro Ala Asn Ile Gln Gln Phe
            195                 200                 205

Glu His Ile Val Pro Leu Arg Arg Val Leu Thr Thr Ala Thr Ile Thr
        210                 215                 220

Leu Leu Pro Asp Ala Glu Arg Phe Ser Phe Pro Arg Val Ile Asn Ser
225                 230                 235                 240

Ala Asp Gly Ala Thr Thr Trp Phe Phe Asn Pro Val Ile Leu Arg Pro
                        245                 250                 255

Asn Asn Val Glu Val Glu Phe Leu Leu Asn Gly Gln Ile Ile Asn Thr
                260                 265                 270

Tyr Gln Ala Arg Phe Gly Thr Ile Val Ala Arg Asn Phe Asp Thr Ile
            275                 280                 285

Arg Leu Ser Phe Gln Leu Met Arg Pro Pro Asn Met Thr Pro Ala Val
        290                 295                 300

Ala Val Leu Phe Pro Asn Ala Gln Pro Phe Glu His His Ala Thr Val
305                 310                 315                 320

Gly Leu Thr Leu Arg Ile Glu Ser Ala Val Cys Glu Ser Val Leu Ala
                        325                 330                 335

Asp Ala Ser Glu Thr Leu Leu Ala Asn Val Thr Ser Val Arg Gln Glu
                340                 345                 350

Tyr Ala Ile Pro Val Gly Pro Val Phe Pro Pro Gly Met Asn Trp Thr
            355                 360                 365

Asp Leu Ile Thr Asn Tyr Ser Pro Ser Arg Glu Asp Asn Leu Gln Arg
        370                 375                 380

Val Phe Thr Val Ala Ser Ile Arg Ser Met Leu Ile Lys
385                 390                 395

(2) INFORMATION FOR SEQ ID NO:19:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:19:

```
Thr Met Asn Gly Asn Glu Phe Gln Thr Gly Gly Ile Gly Asn Leu Pro
1               5                   10                  15

Ile Arg Asn Trp Asn Gly Cys
                20
```

(2) INFORMATION FOR SEQ ID NO:20:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (xi) SEQUENCE DESCRIPTION: SEQ ID NO:20:

```
Ser Arg Asn Ile Val Tyr Thr Arg Ala
1               5
```

(2) INFORMATION FOR SEQ ID NO:21:

(i) SEQUENCE CHARACTERISTICS:
        (A) LENGTH: 24 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:21:

```
Asn Ile Ala Pro Ala Ser Ile Ala Ser Arg Asn Ile Ala Tyr Thr Arg
1               5                   10                  15

Ala Cys Pro Asn Gln Asp Ile Ala
                20
```

(2) INFORMATION FOR SEQ ID NO:22:

(i) SEQUENCE CHARACTERISTICS:
        (A) LENGTH: 24 amino acids
        (B) TYPE: amino acid
        (C) STRANDEDNESS: single
        (D) TOPOLOGY: linear (xi) SEQUENCE DESCRIPTION: SEQ ID NO:22:

```
Asn Ile Val Pro Val Ser Ile Val Ser Arg Asn Ile Val Tyr Thr Arg
1               5                   10                  15

Ala Gln Pro Asn Gln Asp Ile Val
                20
```

(2) INFORMATION FOR SEQ ID NO:23:

(i) SEQUENCE CHARACTERISTICS:
        (A) LENGTH: 24 amino acids
        (B) TYPE: amino acid
        (C) STRANDEDNESS: single
        (D) TOPOLOGY: linear (xi) SEQUENCE DESCRIPTION: SEQ ID NO:23:

```
Asn Ile Ala Pro Ala Ser Ile Val Ser Arg Asn Ile Val Tyr Thr Arg
1               5                   10                  15

Ala Gln Pro Asn Gln Asp Ile Ala
                20
```

(2) INFORMATION FOR SEQ ID NO:24:

(i) SEQUENCE CHARACTERISTICS:
        (A) LENGTH: 21 amino acids
        (B) TYPE: amino acid -continued

```
        (C) STRANDEDNESS: single
        (D) TOPOLOGY: linear (xi) SEQUENCE DESCRIPTION: SEQ ID NO:24:

Thr Met Asn Gly Asn Glu Phe Gln Thr Gly Gly Ile Gly Asn Leu Pro
1               5                  10                  15

Ile Arg Asn Trp Asn
            20
```

ROTAVIRUS PEPTIDE COMPOSITIONS AND METHODS OF USE

CROSS-REFERENCE TO RELATED APPLICATIONS

This application is a continuation of application Ser. No. 07/661,859, filed Feb. 27, 1991, now abandoned, which is a continuation-in-part of application Ser. No. 07/626,041, filed Dec. 10, 1990, now abandoned, which is a continuation-in-part of application Ser. No. 07/552,350, filed Jul. 12, 1990, now abandoned, which is a continuation of application Ser. No. 07/241,761, filed Sep. 7, 1988, now abandoned, which is a continuation of application Ser. No. 06/903,325, filed Sep. 3, 1986, now abandoned, which is a continuation-in-part of application Ser. No. 06/813,661, filed Dec. 26, 1985, now abandoned.

TECHNICAL FIELD

The invention relates to peptides which are useful as vaccines and immunogens capable of simulating neutralizing antibodies against rotavirus. In particular, the invention concerns the epitopic regions of rotavirus proteins VP7, VP6 and VP4 (VP3) which have been formulated into vaccines.

BACKGROUND ART

Rotaviruses are important causes of gastrointestinal disorders and diarrhea in avian and animal species, including man. There are at least eleven known serotypes of rotavirus, some of which are found in humans and others found in various animals and birds. There appears to be some cross-protection among strains, but this is not complete. A number of the important capsid proteins have been sequenced and show considerable homology among serotypes.

The rotavirus genome is thought to consist of eleven segments of double-stranded RNA regardless of the strain. A designation system for the proteins encoded by these segments and present in the intact virus has been proposed, but has not remained constant over the years. There appear to be three proteins associated with the inner shell (VP1, VP2, and VP6) and three associated with the outer capsid. Of interest herein are the inner capsid protein VP6 and two of the outer capsid proteins, VP7 and VP4 (designated VP3 in former nomenclature).

(In various rotaviruses, the absolute order of the genomic fragments does not always conform to the same genes; for example in rotavirus strains SA11, W, and Wa, gene 9 codes for VP7, while in rotavirus strains DS-1, and UK bovine rotavirus (BRV) gene 8 codes for VP7. Also, especially for bovine and human rotavirus, there are variations in the mobility of proteins derived from different isolates originating from the same species. However, the identity of the various virus proteins (VP) designated by the foregoing designations is not in doubt for any particular species.)

As the invention concerns vaccines comprised of epitopes from VP7, VP4 and VP6, further descriptions of these particular proteins are provided as follows:

The major glycoprotein of the outer shell, VP7, has an approximate apparent molecular weight of 38.2 kd in its unreduced form and 41.9 kd in its reduced form and has been shown to be the major antigen responsible for inducing neutralizing antibodies to the virus, and for attachment to cells. A 14 kd fragment of this protein from BRV was also shown to raise neutralizing antibodies against the virus. (Sabara, M., et al., *J Virol* (1985) 53:58–66). Regions of conservation among strains infecting human and animal species in this protein have been reviewed by Estes, M. K., et al., *Microbiol Rev* (1989) 53:410–449. The complete amino acid sequence of rotavirus VP7 glycoprotein for three strains of rotavirus, and a partial sequence for a fourth strain are shown in FIG. 1.

Gunn, P. R., et al., *J Virol* (1985) 54:791–797, investigated various putative antigenic determinants in VP7 of the SA11 serotype. These authors compared the amino acid sequences of the VP7 protein of SA11, NCDV, S2 and Wa serotypes. They investigated the immunogenicity of peptides corresponding to positions 66–76; 90–103; 174–183; 208–225; 247–259; and 275–295 conjugated to keyhole limpet hemacyanin (KLH) using 1-ethyl-(3,3-dimethylaminopropyl) carbodiimide (EDCI) with mixed results. All of the peptides were capable of generating antisera immunoreactive with the immunizing peptides themselves and the denatured form of VP7. However, high titer polyclonal neutralizing antiserum directed against the whole SA11 virus did not recognize any of the seven peptides when they were immobilized on microtiter dishes, pretreated with glutaraldehyde. Further, in a virus neutralization assay, where control polyclonal antiserum prepared against whole virus had a neutralization titer of $10^6$ U/ml, none of the peptide antisera showed significant neutralizing activity. Further, none of the sera recognized whole virus in solid phase RIA. The authors concluded that in the native virus the regions represented by these peptides were not properly exposed, and suggested the possibility of the antigenic sites being composed of discontinuous determinants.

The various serotypes of rotavirus are defined by the neutralizing activity stimulated by VP7; on this basis, eleven serotypes have been identified, six of which are found in humans.

VP4 (formerly called VP3) is also an outer capsid protein and has an approximate apparent molecular weight of 82 kd in unreduced form and 84 kd in reduced form. FIG. 3 shows the amino acid sequences of two strains of rotavirus—C486 which is a bovine strain and SA11 which is a simian-infecting strain.

The inner capsid protein of interest herein is VP6 which is a 45 kd molecular weight protein. Antibodies raised against VP6 appear to be the most cross-species reactive among those raised to viral proteins. The nucleotide sequence and deduced amino acid sequence of the SA11 VP6 protein, as disclosed by Estes et al., Nucleic Acids Res (1984) 12:1875–1887 is shown in FIG. 3. In addition to being itself immunogenic, VP6 has been shown, at least partially by virtue of its abilities to form aggregates of various shapes, to be a superior carrier for other haptens. This is disclosed EPO application 87/3077465.

The present invention provides subunit peptide vaccines corresponding to the epitopic regions of VP7, VP4, and VP6 which are effective as vaccines in that they show demonstrated protection against challenge and/or elicit the production of neutralizing antibodies. The use of these subunit vaccines confers a number of advantages, including safety, economy, and effectiveness.

DISCLOSURE OF THE INVENTION

The invention is directed to peptide subunits derived from VP7, VP4, and VP6 of various rotavirus strains which are capable of producing neutralizing antibodies and are effective as vaccines. Specifically, the invention is directed to peptide-based vaccines which include as an active ingredient a peptide having an amino acid sequence corresponding to positions 275–295 of VP7 from various strains and to similar compositions capable of raising neutralizing antibodies which contain, as active ingredient, a peptide derived from positions 247–259 of these proteins. Similar vaccines and antibody-producing compositions which contain as active ingredient the peptide representing positions 232–255 or 240–248 of the VP4 protein, and similar compositions of matter containing as active ingredient the peptide corresponding to positions 40–60 of VP6 are included in the invention. The peptide derived from the sequence at positions 232–255 or 240–248 of VP4 corresponds to the trypsin cleavage site and can compete with the virus for trypsin to interfere with infectivity. Compositions containing these peptides can thus also be used therapeutically and as prophylactics in preventing infection.

The invention is, therefore, directed to compositions of matter containing these peptides, including pharmaceutical and vaccine compositions, and to methods to immunize and treat (therapeutically and prophylactically) animal subjects with these materials.

BRIEF DESCRIPTION OF THE DRAWINGS

FIGS. 1(*a–c*) shows the amino acid sequences of several rotavirus VP7 glycoproteins (SEQ ID NO:12), (SEQ ID NO:13), (SEQ ID NO:14), (SEQ ID NO:15).

FIG. 2 shows the amino acid sequences of the VP4 proteins from the bovine C486 strain and the simian SA11 rotavirus strain (SEQ ID NO:16) and (SEQ ID NO:17).

FIG. 3(*a–b*) shows the nucleotide sequence and deduced amino acid sequence of the VP6 protein from SA11 (SEQ ID NO:18) and (SEQ ID NO:19)

FIG. 4 shows the production of antibodies by administration of VP7 glycoprotein or its 14 kd fragment.

FIG. 5 shows the ability of VP7 subunits 247–259 and 275–295 to block virus attachment to host cells.

FIG. 8 shows the ability of the 232–235 peptide from VP4 to inhibit cleavage of VP4 by trypsin.

MODES OF CARRYING OUT THE INVENTION

Figure 6:
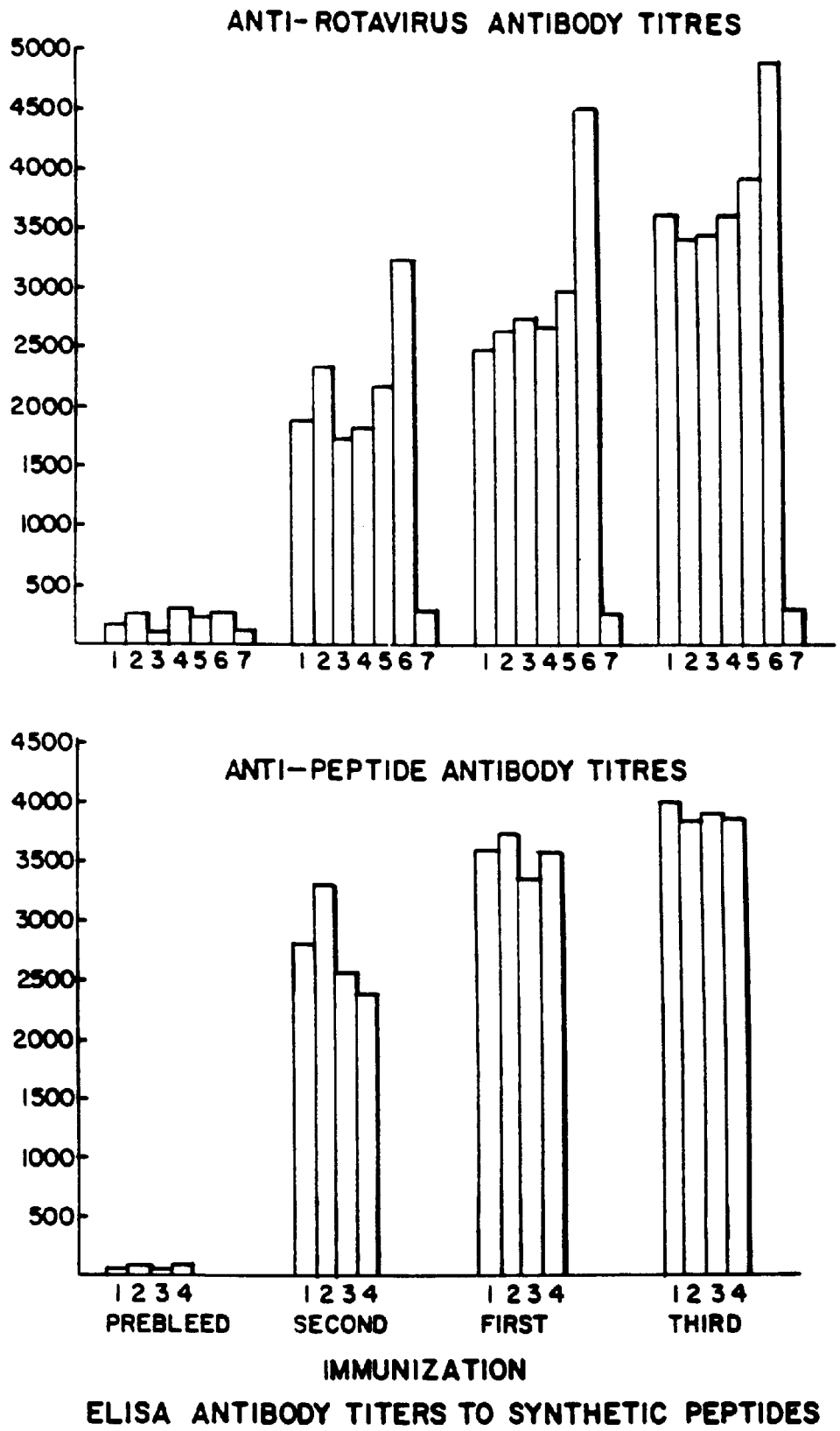
FIG. 6 shows the ability of the VP7 subunits to elicit antiviral peptides by ELISA analysis.

The invention provides short peptide subunit sequences which are effective active ingredients in vaccines. There are five subunits of the rotavirus peptides which are the subject of the present invention. These are the peptides represented by positions 232–255 or 240–248 of the VP4 protein; a subunit representing positions 40–60 of VP6; and peptides representing position 247–259 or positions 275–295 of VP7. These peptides are represented herein by the designations "232–255"; "240–248"; "40–60"; "247–259"; and "275–295"; respectively.

As is illustrated in the figures and examples below, and is generally known in the art, certain conservative amino acid substitutions can be made in these peptides without affecting their immunological activity. Specifically, for example, FIG. 1 shows that even in the highly conserved region of VP7 at positions 275–295, the four strains illustrated show some differences; at position 278, for example, Val, Ala, and Thr appear to be interchangeable; at position 281 Val and Thr; at position 284, Ile and Met. Thus, such conservative changes, especially with regard to relatively nonpolar amino acids Thr, Met, Val, Ile, Leu, and Ala, appear to be tolerated. This is also demonstrated in Examples 7 and 8 wherein the apparent immunogenicity and trypsin susceptibility of the VP4 subunit 232–255 is not altered by the substitution of alanine residues in the synthesized peptide for the valine residues in the native protein. Accordingly, the designations "232–256,""275–295, " etc., designate not only those sequences which occur natively in the various serotypes of rotavirus, but also include conservative amino acid substitutions of the type just mentioned, where the nonpolar residues set forth above are readily interchangeable.

Furthermore, these designations include both the discrete peptide referred to, and these peptides which are included within larger proteins wherein the remainder of the sequence is not derived from the corresponding rotavirus protein. Thus, for instance, the designation "275–295" includes proteins which contain this sequence, but wherein the additional sequence is nowhere found in the VP7 protein of any rotavirus.

A typical occurrence of such additional peptide lies in the synthesis of extended forms of the relevant antigenic portion by sequence intended to facilitate linkage to a carrier. Commonly a cysteine residue may be added to the N- or C-terminus or even inserted within the relevant sequence (see, for example, Silversides et al., *J Reprod Immunol* (1988) 13:249–261) to provide a sulfhydryl group for reactivity to commercially available linkers such as those available from Pierce Chemical Co., Rockford, Ill. As the Silversides article shows, even interruption of the antigenic sequence with the cysteine residue does not destroy the antigenic or immunogenic properties of the peptide. The cysteine residue linked to the N- or C-terminus may also be spaced from the antigenic region by one or more amino acid residues, usually those of, for example, alanine or glycine, which have relatively inconsequential sidechains. These extensions are also included in the illustrated peptides below.

Furthermore, these peptides include embodiments wherein the relevant antigenic region, denoted by the numbers, is present in a repeated motif, either a tandem repeat directly coupled through amide linkages or separated by additional nonrotavirus derived sequence. The repetition of the relevant antigenic sequence or the inclusion of additional nonrotaviral peptide as a fusion protein in many cases enhances the immunogenicity of the peptide.

Consistent with the foregoing, a peptide which consists essentially of an amino acid sequence "substantially equivalent" to positions 275–295 of rotavirus VP7 viral protein includes peptides which have the sequence of amino acids 275–295 of any naturally occurring rotavirus, as well as such peptides wherein one or more nonpolar amino acids has been replaced by a conservative substitute from among the group set forth above, and which retain the antigenic characteristics of the naturally occurring sequence. By "antigenic characteristics" is meant the ability to crossreact with antibodies raised against the naturally-occurring sequence. "Consists essentially of" refers to the possibility that the peptide contains 1–4 additional amino acids (e.g., cys) which facilitate conjugation to carrier as illustrated in the examples below.

Similar definitions apply with respect to the other four subunit peptides of the invention.

By the term "protein having as its sole antigenic determinant the amino acid sequence substantially equivalent to positions 275–295 of rotavirus VP7" is meant a protein wherein the sequence represented by positions 275–295, defined as set forth above, is the only rotavirus sequence of the parent protein (in this case VP7) included in the protein. Thus, such proteins would include longer chain moieties where additional, non-VP7 sequence is included along with either the sequence found in these positions in wild-type VP7, or the conservatively substituted, antigen characteristic retaining sequences described above. Such additional protein might include, for example, a binding protein as described in examples 5 and 6, an additional fusion protein derived from bacteria which might act as an immunogenic carrier, or additional sequence which would be useful in purification, etc. As above, similar definitions apply with respect to the other four subunit peptides of the invention.

The invention subunit peptides, as described above, are useful as vaccines for protection of animal and avian subjects against infection by rotavirus. As these invention peptides represent relatively short portions of the viral proteins from which they are derived, it is generally preferred, when the peptides per se are used, to enhance their immunogenicity by coupling them to carriers. Such coupling can be done using conventional protocols using covalent conjugation to traditional carriers such as BSA or keyhole limpet hemocyanin (KLH), the *E. coli* pilin protein K99 or preferably to the particulate form of VP6 from rotavirus. The conjugation can also be effected by creation of fusion proteins using recombinant techniques wherein the peptide which comprises the active portion is made a part of a larger recombinant peptide containing, other than the region represented as the epitope and described herein, only nonrotaviral sequences. Furthermore, the active epitopic regions can be prepared as tandem repeats. In addition, the peptide active ingredients can be fused to, or otherwise conjugated to a binding peptide for protein/protein binding to the VP6 carrier as described in the above-referenced copending applications and as wet forth hereinbelow.

In addition to the peptide active ingredient which may be conjugated to carrier, invention compositions may include an immunostimulant or adjuvant, such as complete Freund's adjuvant, aluminum hydroxide, and liposomes. The active ingredients can be formulated using generally known methods to prepare pharmaceutically useful compositions such as those described in *Remington's Pharmaceutical Science*, Mack Publishing Co., Easton, Pa. (latest edition). These compositions contain an effective amount of the active ingredient peptide together with a suitable amount of carrier vehicle. Other descriptions of preparation of vaccine formulations may be found in "New Trends and Developments in Vaccine," Voller, A., et al., University Park Press, Baltimore, Md. (1978).

The vaccines can be administered in generally recognized manner, generally systemically through injection; however, other effective means of administration are included within the scope of the invention. Dosage levels depend on the mode of administration, the nature of the subject, and the quality of the carrier/adjuvant formulation. Typical amounts are in the range of 1 µg–1 mg/kg. Preferred amounts are in the range of 50–100 µg/kg. Multiple administration to immunize the subject is preferred, and protocols are those standard in the art adapted to the subject in question.

The invention peptides are also useful as diagnostic tools to detect the presence or absence of rotaviral infection. For use in such protocols, standard immunoassay procedures can be used to detect the presence of antirotaviral antibodies in a fluid sample from the subject to be tested. In these procedures, the sample is contacted with the peptide in order to form an immunocomplex, and the formation of the complex is then detected as a measure of the presence of antibodies. A wide variety of protocols including immunoprecipitation, agglutination, and solid support assays can be adapted to this utility.

For all of the foregoing utilities, varying amounts of cross-reactivity among strains and serotypes has been found, as will be clear from the examples below.

Therefore, the peptide subunits and proteins containing them may have variable efficacy depending upon the level of cross-reactivity with strains other than those from which they are specifically derived. It may be desirable in some instances to supply cocktails of specific sequences derived from more than one strain in order to provide cross-reactivity if desired.

The peptide subunits of the VP4, 232–255 and 240–248, also can be used for prophylactic protection or for therapy with respect to rotaviral infection. As illustrated in Examples 8 and 9 below, the peptide subunit represents the trypsin cleavage region of the VP4 and can compete with intact VP4 for the enzyme; the peptides are also demonstrated to be capable of plaque reduction and prophylactic protection of suitable subjects. Thus, prophylactic and therapeutic compositions containing peptides with these regions as the sole antigenic determinant or peptides consisting essentially of these sequences can be formulated according to standard art-recognized procedures for prophylaxis and therapy.

In general, administration of such therapeutic and prophylactic compositions is systemic, including administration by injection and transmucosal or transdermal administration, or the compositions can be administered orally. For oral administration, delivery in a formulation protective against the low pH of the stomach and/or the proteolytic action of the small intestine is desirable. Such formulations, such as enteric or capsular formulations may be found for example, in *Remington's Pharmaceutical Sciences*, (supra). Typical dosage ranges for prophylactic or therapeutic use of these subunits is in the range of 500 μg/kg–500 mg/kg, preferably 500 μg/kg–200 mg/kg, more preferably 50 μg/kg–20 mg/kg. These are dosage estimates, and the actual range is determined by the nature of the subject, the level of the challenge, the mode of administration, and the judgment of the practitioner. Thus, dosage values outside the suggested range are also included within the scope of the invention.

The following examples are intended to illustrate but not to limit the invention.

EXAMPLE 1

Immunogenicity of the "14K" Fragment of VP7

The ability of the 14K subunit VP7 effectively to mimic the total protein effect when injected into mice was illustrated as follows:

A bovine rotavirus (isolate C486, subclone 13) was propagated in MA-104 cells and purified by centrifugation. The 14 kd polypeptide fragment was prepared by in situ enzyme digestion of the 38.2 kd glycoprotein as described by Cleveland, D. W., et al., *J Biol Chem* (1977) 25:1102–1106. A gel strip containing the 38.2 kd VP7 glycoprotein was placed into the well of a 5% stacking/20% resolving polyacrylamide gel. A 13 cm×1 cm gel strip was treated with papain (Calbiochem-Boehring, San Diego, Calif.) at a concentration of 130 μg/cm of gel since this gave the best yield of the 14 kd polypeptide.

Prestained molecular weight markers were used in order to visualize the time of maximum resolution between the 14.3 kd and 18.4 kd markers. The 14 kd peptide fragment was then electroeluted from gel slices, and a protein determination performed. Confirmation of the authenticity and purity of the peptide was by examination of its profile on polyacrylamide gels and by its reaction with monoclonal antibody from hybridoma 11D12–6.

The electroeluted 14 kd polypeptide was then lyophilized and a portion of the preparation was conjugated to bovine serum albumin (BSA) as follows. One mg of peptide was dissolved in 125 μl of 0.1 M PBS pH 7.4. The BSA solution was prepared by dissolving 1.25 mg BSA in 600 μl 0.1 M PBS pH 7.4 and to this were added dropwise 250 μl of a 2.5 M glutaraldehyde solution and the peptide solution consecutively over 15 minutes. The reaction mixture was gently agitated for 24 hours at room temperature and then dialyzed extensively against sterile distilled water. Lyophilization of the conjugated peptide yielded a pinkish powder which was stored in desiccant at −20° C.

Groups of ten mice (Charles River, Wilmington, Mass.) were immunized with either the unconjugated 14 kd peptide, BSA-conjugated 14 kd peptide, infectious double-shelled virus, or purified VP7 according to the protocol outlined in Table 1.

TABLE 1

Schedule for Mice Immunized with 14K Peptide, VP7 and Infectious Virus

| Groups/Immunogen | | 1 | | | DAYS |
|---|---|---|---|---|---|
| 51 | $61^2$ | 68 | 8 | 31 | 37 44 |
| A. Unconjugated 14 kd | Prebleed | 13.6 μg; | 13.6 μg; | Bleed |
| 13.6 μg; | Bleed | 0.675 μg | Bleed | | |
| I.P.; F.I. | | I.P.; F.C.$^1$ | I.P.; F.I | | I.P.; F.I. |
| B. Conjugated | 14 kd | " | 13.6 μg | 13.6 μg | " 13.6 μg |
| " | 0.675 μg | " | | | |
| I.P.; F.I. | | I.P.; F.C. | I.P.; F.C. | | I.P.; F.I. |
| C. Glycoprotein | VP7 | " | 4.5 μg | 4.5 μg | " 4.5 μg |
| " | 0.675 μg | " | | | |
| I.P.; F.I. | | I.P.; F.C. | I.P.; F.C. | | I.P.; F.I. |
| D. Infectious virus | | " | 0.675 μg | 0.675 μg | " 0.675 μg |
| " | 0.675 μg | " | | | |
| I.P.; F.I. | | I.P.; F.C. | I.P.; F.I. | | I.P.; F.I. |
| E. Negative Control | | " | saline; | saline; | "saline;" |
| $E_1$-0.675 μg | " | | | | |
| I.P.; F.I. | | I.P.; F.C. | I.P.; F.I. | | I.P.; F.I. |
| | | | | | $E_1$-saline; " |
| | | | | | I.P.; F.I. |

$^1$The quantities given are per mouse (10 mice per group); I.P. = intraperitoneal; F.C. = Freund's Complete Adjuvant.
$^2$All mice, except 5 mice in group $E_2$ were boosted with infectious virus.

The quantities of antigen to be administered were determined on an equimolar basis. Antibody responses to the different antigens were characterized by ELISA and immunoblot ELISA using bovine rotavirus (isolate C486 subclones 12 and 13) as the antigen and by serum neutralization assays.

As illustrated in FIG. 4 (upper panel), there was a significant antibody response to all the antigens used. Noteworthy is the similarity in response between the total 38.2 kd VP7 glycoprotein and the 14 kd peptide fragment. It also appears that conjugation of the 14 kd polypeptide to a carrier was not necessary to induce a good antibody response. This may be due to the large size of the polypeptide fragment thereby increasing the probability of its containing both B-cell and T-cell determinants.

To investigate the possibility of the 14 kd fragments priming an immune response, animals which had been immunized with the 14K fragments were boosted at 61 days with infectious, double-shelled virus. These animals showed an additional, but minor, response after the infectious virus was administered (68 days).

The antibodies produced in the foregoing protocol had neutralizing ability. Sera from all groups administered 14 kd peptide, VP7, or virus possessed neutralizing antibodies (FIG. 4, lower panel). The best response was produced by animals immunized with infectious virus (Group D). Total antibody titers are measured by ELISA and neutralizing antibody titers were similar for both the conjugated and unconjugated form of the 14 kd peptide.

At 68 days, after all the groups had been exposed to infectious virus, the neutralizing antibody titer increased slightly over that seen at 51 days, suggesting that each subsequent exposure further stimulates the immune response, or alternatively, there may abe other antigens in the infectious virus that are capable of inducing a neutralizing response. The presence of antibodies to the 45 kd protein VP6 was shown by immuno-blot ELISA reactions at 68 days; however, antibodies to the 84 kd VP4 protein could not be detected.

Immunoblot ELISA reactions of sera from selected animals in each group at 37, 51 and 68 days showed that all the sera, except those obtained prior to immunization and the negative control group (E), possessed antibodies to VP7. Antipeptide antibodies produced to 14 kd peptide from clone 13 were also immunoreactive with VP7 from clone 12 although the mRNA encoding VP7 from these species is not identical. The similar intensity displayed by the reaction of the glycoprotein species with antipeptide antibodies suggests that the 14 kd polypeptide may represent an immunodominant region of the glycoprotein.

EXAMPLE 2

Localization of the 14 kd Peptide

The 14 kd peptide is characterized in that it has i) a carbohydrate moiety, ii) extensive disulfide bridging, iii) relatively conserved region(s) among different rotavirus serotypes, iv) hydrophilic areas, and v) potential immunogenic regions. In addition, the cleav-age patterns obtained by partial proteolysis of the glycoprotein using chymotrypsin, *S. aureus* V8 protease, papain and cyanogen bromide permitted the localization of the fragment from the known amino acid sequences shown in FIG. 1. The amino acid sequence of Nebraska calf diarrhea virus (NCDV bovine rotavirus), which exhibits high nucleic acid homology with the C486 bovine rotavirus and is of the same serotype, was used to map the 14K polypeptide fragment to the region spanning amino acids 165–295. The position of this fragment is shown boxed in this figure.

EXAMPLE 3

Subunit Immunogens of VP7

A hydrophilicity plot of the corresponding NCDV glycoprotein identified several hydrophilic regions within this area. Based on this, four peptides, corresponding to amino acid residues 175–183; 179–183 and 251–259 spliced together; 247–259; and 275–295 of bovine rotavirus VP7 were synthesized by the solid-phase peptide synthesis method of Merrifield.

The specific amino acid sequence of each peptide is as follows:

```
Peptide175–183: Tyr-Gln-Gln-Thr-Asp-Glu-Ala-Asn-Lys (SEQ ID NO: 1)

Peptide(179–183)-(251–259): Asp-Glu-Ala-Asn-Lys-Lys-
Leu-Gly-Pro-Arg-Glu-Asn-Val-Ala (SEQ ID NO: 2)

Peptide247–259: Arg-Asn-Cys-Lys-Lys-Leu-Gly-Pro-Arg-
Glu-Asn-Val-Ala (SEQ ID NO: 3)

Peptide275–295: Pro-Thr-Thr-Ala-Pro-Gln-Thr-Glu-Arg-
Met-Met-Arg-Ile-Asn-Trp-Lys-Lys-Trp-Trp-Gln-Val. (SEQ ID NO: 4)
```

The purity of each peptide was assessed using thin-layer chromatography and reverse-phase high-performance liquid chromatography. Fast atom bombardment mass spectrometry was used to confirm molecular weights.

In addition, the foregoing were coupled to an N-terminal Cys residue to facilitate coupling to carrier.

The reactivity and specificity of the synthetic peptides were determined by ELISA using either anti-VP7 monospecific VP7 serum or monoclonal antibodies specific for the various regions of VP7 and by adsorption blocking assays. Table 2 shows the results of the ELISAS. As shown in the table, while all of the peptides were immunoreactive with the antiserum, only the peptides representing positions 247–259 and 275–295 were specifically immunoreactive with monoclonals directed to particular determinants.

TABLE 2

Reactivity[a] of Monoclonal Antibodies and Monospecific Serum
With Synthetic Peptides of the 14K Fragment of VP7

| | SYNTHETIC PEPTIDES | | | |
|---|---|---|---|---|
| | p174–183 | p(179–183)–(252–259) | p247–259 | p275–295 |
| Monospecific anti-glycoprotein (VP7) serum | 2,500[a] | 5,000 | 1,000 | 1,250 |
| Monoclonal antibodies | | | | |
| 4B5-5 | 50 | 50 | 5,000 | 50 |
| 11D10-4 | 10 | 250 | 4,000 | 100 |
| 11D12-6 | 10 | 50 | 100 | 8,500 |
| 10D207 | 10 | 50 | 20 | 10,000 |

[a]Antibody titers were determined by ELISA and are expressed as the reciprocal of the dilution giving a 50% end point.

FIG. 5 shows the results of the assay for ability of the peptides to inhibit attachment of virus to MA104 cells; again, only peptides representing positions 247–259 and 275–295 were able to block virus attachment to these cells.

For testing immunogenicity, the peptides were conjugated to carrier. Peptide 175–183 was conjugated to keyhole limpet hemocyanin (KLH) via a bis-diazotized toluidine linkage that produces N-terminally bound peptides. The other three peptides were conjugated to KLH via N-maleimidobenzoyl-N'-hydroxysuccinimide ester through the N-terminal Cys residue producing N-terminally bound peptide conjugates. Each of the conjugates was administered to groups of 10 CD-1 mice according to the schedule outlined in Table 3.

TABLE 3

Immunization Schedule for Mice Injected
with Synthetic Peptides Within 14K of VP7

| Group Designation | 0 | 1 | 2 | 3 |
|---|---|---|---|---|
| 1 p175–183 | Pre-bleed | –100 μg; FC[a] | — | — |
| 2 p(179–183)–(251–259) | Pre-bleed | –100 μg; FC | — | — |
| 3 p247–259 | Pre-bleed | –100 μg; FC | — | — |
| 4 p275–295 | Pre-bleed | –100 μg; FC | — | — |
| 5 p175–183 p(175–183)–(251–259) p247–259 p275–295 | Pre-bleed | –25 μg; FC –25 μg; FC –25 μg; FC –25 μg; FC | — | — |
| 6 Infectious Virus | Pre-bleed | –1.6 μg; FC | — | — |
| 7 Controls | Pre-bleed | -saline; FC | — | — |

| Group Designation | 4 | 5 | 6 | 7 |
|---|---|---|---|---|
| 1 p175–183 | -bleed –100 μg; FI[a] | — | -bleed –100 μg; FI | -bleed |
| 2 p(179–183)–(251–259) | -bleed –100 μg; FI | — | -bleed –100 μg; FI | -bleed |
| 3 p247–259 | -bleed –100 μg; FI | — | -bleed –100 μg; FI | -bleed |
| 4 p275–295 | -bleed –100 μg; FI | — | -bleed –100 μg; FI | -bleed |
| 5 p175–183 p(175–183)–(251–259) p247–259 p275–295 | -bleed –25 μg; FI –25 μg; FI –25 μg; FI –25 μg; FI | — | -bleed –25 μg; FI –25 μg; FI –25 μg; FI –25 μg; FI | -bleed –25 μg; FI –25 μg; FI –25 μg; FI –25 μg; FI |
| 6 Infectious Virus | -bleed –1.6 μg; FI | — | -bleed –1.6 μg; FI | -bleed –1.6 μg; FI |
| 7 Controls | -bleed -saline; FI | — | -bleed -saline; FI | -bleed -saline; FI |

[a]FC = Freund's Complete Adjuvant;
FI = Freund's Incomplete Adjuvant.

Each mouse in Groups 1 to 4 of Table 3 was given 100 μg of each KLH-conjugated peptide in Freund's adjuvant. Group 5 was given 25 μg of each of the four KLH-conjugated peptides in Freund's Adjuvant. Group 6 received 1.6 μg of infectious double-shelled rotavirus and Group 7 represented the negative control group which received saline plus Freund's Adjuvant. The antigen preparations were administered three times over a six-week period and mice were bled prior to each immunization.

The sera were titrated using ELISA with either double-shelled rotavirus or to the individual peptides which had been used for immunization. In FIG. 6, all of the peptides were capable of eliciting an antibody response which was antigenic to the virus (upper panel) or to the peptide itself (lower panels).

EXAMPLE 4

Production of Neutralizing Antibodies by VP7 Subunits

The sera obtained in Example 3 were tested for their ability to neutralize the infectivity of the bovine rotavirus isolate C486 using a standard 50% plaque reduction assay. In this assay, virus dilutions representing 30–50 PFU were mixed 1:1 with various dilutions of antibody and incubated for 1 hour at 37° C. Virus attachment to MA104 monolayers was allowed to proceed at 37° C. for 2 hours before the virus inoculum was removed; the cells were washed with MEM and then overlaid with 1.6% Bacto-agar (Difco) diluted in MEM and supple-mented with 5 µg of pancreatin per ml, 0.7% of a 1:1000 neutral red stock solution, and 0.1% DEAE-dextran. Plaques appeared after 5 to 6 days of incubation at 37° C.

Figure 7:
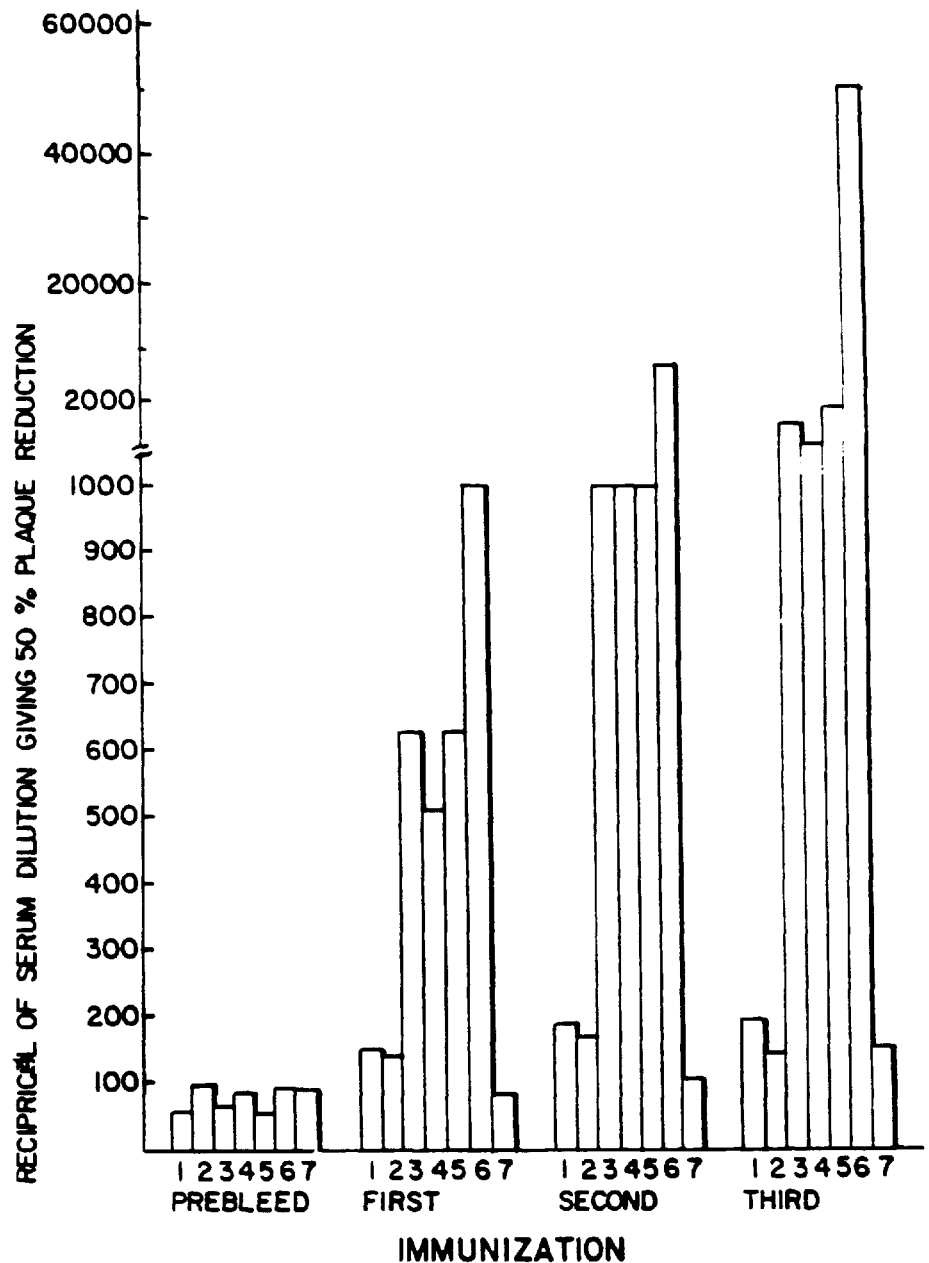
FIG. 7 shows the ability of vaccines comprising the peptides 247–249 and 275–295 derived from VP7 to produce virus-neutralizing antibodies.

As shown in FIG. 7, peptide 247–259, peptide 275–295 and the mixture of the four peptides induced virus-neutralizing antibodies which increased after each immunization.

A passive antibody transfer experiment was also used to predict ability to raise protective responses. Monoclonal antibody 10D2-7, which specifically recognizes synthetic peptide 275–295 (Table 2) was used to provide passive protection. The protocol and results of this study are outlined in Table 4.

TABLE 4

Passive Antibody Transfer of Monoclonal Antibody 10D2-7

| Group Designation | Time 0[a] Preparations | Time 1[a] Preparations | Titer[b] (PFU/mL) | Diarrhea[c] |
|---|---|---|---|---|
| I | 1:50 dilution of Mab 10D2-7 | $5 \times 10^6$ PFU/ml mouse rotavirus | $3.5 \times 10^2$ PFU/ml | ± |
| II | 1:50 dilution of MAB 10D2-7 mixed with $5 \times 10^6$ PFU/ml of mouse rotavirus 1 hour prior to administration | MEM | $5 \times 10^1$ PFU/ml | − |
| III | MEM | $5 \times 10^6$ PFU/mL mouse rotavirus | $4 \times 10^5$ PFU/ml | + |
| IV | MEM | MEM | 0 | − |

[a]Time 0 and Time 1 preparations were made as described above. 100 µl of the preparations were administered by tubing to the stomach of each neonate.
[b]PFU/ml = plaque-forming units of rotavirus per ml of intestinal homogenate.
[c]Diarrhea was assessed by the color and consistency of the fecal material compared to the control groups (III and IV).

Four groups each consisting of ten 7-day-old mice were first separated from their mothers for 2 hours and then given the indicated Time 0 preparations by tubing to the stomach. Approximately 1 hour later they were given the Time 1 preparation. The mice were kept at 33° C. for 8 hours with constant monitoring of fecal consistency. After 8 hours, the mice were sacrificed and their intestines removed and pulverized. The amount of infectious virus in the intestine was determined by 50% plaque-reduction assay.

Mice in Group III which did not receive mono-clonal antibody were not protected. They became diarrhetic and had 5 logs of rotavirus in intestinal homogenates prepared 8 hours after challenge. There was a significant reduction in the amount of diarrhea and in the level of virus in intestinal homogenates of mice in Group I (given monoclonal antibody orally before challenge with virus) and Group II (challenged with a mixture of monoclonal antibody and virus).

EXAMPLE 5

Preparation of Conjugates with 275–295 VP7 Subunit

Additional peptides representing positions 275–295 of the VP7 protein were synthesized, which had minor modifications to facilitate conjugation to carrier. To facilitate incorporation with KLH, the 275–295 peptide set forth above in Example 3 was also prepared with a cysteine residue at its carboxy terminus. This peptide is designated 275–295C.

A second 275–295 peptide contains additional sequence at its amino terminus which permits protein-protein interaction with VP6 carrier. This additional peptide has the sequence: Cys-Gly-Ala-Ser-Arg-Asn-Ile-Val-Tyr-Thr-Arg-Ala-Gly-(275–295) (SEQ ID NO:6). The resulting peptide is designated herein BP-(275–295) (SEQ ID NO:6).

The 275–295C peptide was coupled to KLH using the procedure of Green, N., et al., *Cell* (1982) 28:477–487. Briefly, KLH (20 mg) in 1 ml of 0.01 M sodium phosphate buffer, pH 7.2, was stirred with m-maleimidobenzoyl-N-hydroxysuccinimide ester (MBS) (5.1 mg, 25.5 µM dissolved in 500 µl dimethylformamide) at room temperature for one hour. Unreacted MBS was removed by HPLC on Synchropak the GPC-100 gel filtration column (500×10 mm ID), equilibrated with 0.1 M potassium phosphate buffer, pH 6.0, and the conjugate was eluted with the same buffer. The maleimido group bound to KLH was estimated graphically by adding aliquots of L-cysteine to the conjugate and reacting excess cysteine with Ellman's reagent. The 275–295C peptide in 200 µl of 0.1 M PBS, 0.72, was added to a solution of the KLH-MBS conjugate (1 ml) containing approximately 0.5 µM of the maleimido group, and the pH was adjusted to 7.8 with 0.1 N NaOH. The mixture was stirred at room temperature for 12 hours and dialyzed against 0.1 M PBS buffer, pH 7.2. The resulting conjugate is designated 275–295C-KLH as the carrier is bound to the carboxy terminus of the peptide.

Conjugation to the VP6 carrier was achieved in several protocols. Recombinant VP6 used as carrier was prepared as follows:

The construction of recombinant *Autographa californica* nuclear polyhedrosis virus (AcNPV) containing gene 6 from BRV and the assembly of VP6 particles following infection of spodoptera frugiperda (SF9) cells is described by Redmond, M. J., et al., *Mol Immunol* (1990, in press). Briefly, genomic RNA extracted from purified bovine rotavirus strain C486 was used to produce cDNA, which was ligated into the PstI site of pBR322 and used to transform *E. coli* strain DH1. The resulting colonies were probed with radiolabeled cDNA prepared from purified genomic RNA segment 6 as template. The gene 6 cDNA was tailored and ligated into the baculovirus transfer vector pAc373. Rotavirus gene was integrated into the genome of *A. californica* by homologous recombination in *S. frugidperda* (SF9) cells as outlined by Summers, M. D., et al., *Texas Agr Exptl Sta Bull* (1987) 1555:26–27. Recombinants were identified by plaque hybridization using radiolabeled VP6 cDNA described above, plaque purified and analyzed for expression of recombinant gene 6 produced proteins by SDS-PAGE analysis and Western blot.

The recovered virus containing gene 6 was used to infect SF9 cells. Following incubation for 72 hours at 27, the cells were lysed in a 2 ml bicarbonate buffer, pH 7.5, containing 0.05% triton X-100 and 0.2 trypsin inhibitor units per ml, and cellular debris was removed by centrifugation at 1500 g. The supernatant was dialyzed against 0.1 M glycine buffer, pH 2.4, for 24 hours. The dialysis solution was exchanged for 0.01 M citrate buffer, pH 4.0, for 24 hours, and then for 0.01 M tris-HCl, pH 7.4. Dialysis was continued until the protein suspension became clear. The quality of the VP6 spheres produced by this method was determined by electronmicroscopy and purity confirmed by SDS-PAGE.

In one approach, the BP-(275–295) was conjugated to VP6 through protein-protein interaction. In this protocol, the BP-(275–295) and the VP6 carrier were mixed at a 10:1 (w/w) peptide:carrier ratio in 0.1M PBS, pH 6.5 and incubated for 30 minutes at 37° C. The binding peptide and VP6 automatically associate to provide the conjugate, designated VP6-(BP-275–295).

The 275–295 peptide per se was also coupled to VP6 using the routine carbodiimide (EDCI) coupling procedure using a coupling ratio of 10:1 (w/w). This conjugate is designated herein VP6-(275–295).

In all cases, coupling to VP6 was analyzed using SDS-PAGE under nonreducing conditions, indicating an increase in the molecular weight of carrier protein VP6 corresponding to the molecular weight of the coupled peptide. In Western blot assay, the bands reacted with anti-VP6 and anti-rotavirus sera.

In addition to the foregoing, conjugates were prepared using the K99 *E. coil* pilin peptide and the 275–295 VP7 subunit. This conjugate was prepared by first isolating the K99 from *E. coli* pilin by urea extraction and ammonium sulfate precipitation. The conjugation was conducted using the carbodiimide method to yield a conjugate with a peptide:carrier ratio of 3.5:1 as determined by UV spectroscopy, amino acid analysis and gel electrophoresis.

EXAMPLE 6

Protection of Neonates

In initial experiments, the K99-(C275–295) conjugate was used to immunize cows prior to parturition-using 100 μg of the conjugate in DDA-aluminum hydroxide gel. (C275–295) represents the peptide having a Cys residue at its N-terminus and conjugated to carrier through this residue. After one immunization, anti-rotavirus titers determined by ELISA increased from 8–10,000 in two tested cows, to 100,000. No effect on the anti-rotavirus titers was obtained by injection of the carrier alone.

In further experiments, these conjugates as well as the conjugates prepared as set forth in Example 5 were used in an immunization protocol to show their ability to protect mice against challenge. The protocol is as follows: In a primary immunizing dose, the conjugate was emulsified with Freund's Complete Adjuvant;

in the second and third immunizations, emulsification was with Freund's Incomplete Adjuvant, using equal volumes of conjugate and adjuvant in every case. All doses were 50 μg of conjugate. Groups of mice were immunized intramuscularly three times before and after breeding.

The first immunization was given at 7 weeks of age, and the second and third at two-week intervals. Litters were born when the mice were 12–14 weeks old. The mice used were Harlan Sprague-Dawley CD-1 rotavirus-free mice purchased at six weeks of age and weighing 25–30 g. The mice were verified to be seronegative for rotavirus antibodies.

Following birth, the mouse pups were allowed to suckle their dams and were challenged at 7 days of age with one of four rotavirus isolates: Bovine rotavirus strain C-486 (serotype 6), simian rotavirus SA11 (serotype 3), human rotavirus DS-1 (serotype 1), and Wa (serotype 2). All except C-486 were obtained from Dr.

Marta Sabara (Praxis Biologics, New York). C-486 was adapted to grow in MA104 cells (Babiuk, L. A., et al., *J Clin Microbiol* (1977) 6:610–617).

The virus used for challenge was grown in MA104 cells, harvested and concentrated by the method described by Ijaz, M. K., et al. (*Antiviral Res* (1987) 8:283–298). The challenge dose was approximately $10^4$ pfu/mouse, unless otherwise noted, suspended in 100 μl MEM and administered by intubation of the stomach with a soft, flexible plastic feeding tube. Trypan dye was used to assess accuracy of intubation.

The administration of 100 μg of the K99-(C275–295) or KLH-(C275–295) peptide in the presence of either FCA or DDA was evaluated using this protocol. The K99-(C275–295) vaccine gave partial protection against challenge in neonatal mice following three immunizations of their dams resulting in diarrhea scores of ++ (diarrhea scores of ++++ resulted where there was no immunization). Complete protection, comparable to administration of whole virus, was given when KLH-(C275–295) was used. In this experiment, a very high challenge dose ($10^6$–$10^7$ pfu) was used; thus the level of protection afforded is quite significant.

In a second set of determinations, the protective effect of the vaccines prepared from the conjugates described in Example 5 was evaluated using two criteria—the prevention of diarrhea in the pups, and the prevention of decreased xylose adsorption from the intestine.

The appearance of diarrhea was scored clinically up to 72 hours postchallenge using clinical scores as follows:

(0) no sign of diarrhea in live mice, or on necropsy;
(+) no external signs of diarrhea but semi-liquid colon contents at autopsy;
(++) fluid was apparent on palpation of the abdomen and the colon was filled with liquid feces and gas;
(+++) the external anal region was soiled with feces and intestinal fluid was present on palpation;
(++++) liquid feces were present around the anal region and on palpation of the abdomen intestinal fluid was present and oozed from the anus; severe dehydration, internal liquid content in colon and caecum and distention due to accumulation of gas.

Small intestinal infection was measured by a xylose adsorption test 72 hours postchallenge. Mice were given 100 μl of 5% w/v solution of xylose by intubation orally as described above. Two hours later, they were sacrificed by decapitation and blood collected in heparinized Hematocrit tubes. Plasma was collected and assayed for D-xylose as described by Ijaz, M. K., et al., *J Virol Meth* (1987) 18:153–157. Decreased xylose absorption is an indication of intestinal damage due to virus infection.

The results of the immunization are shown in Tables 5 and 6. Table 5 shows the protective effect as measured by clinical criteria; Table 6 shows the results as judged by the xylose absorption test.

TABLE 5

Protection Against Infection (Diarrhea)

| Groups | Immunogen | Diarrheal Score Following Challenge with Rotavirus Isolate | | | |
| --- | --- | --- | --- | --- | --- |
| | | Wa | DS-1 | SA-11 | BRV |
| 1 | Placebo | +++ | +++ | ++++ | ++++ |
| 2 | VP6 | ++ | ++ | +++ | ++ |
| 3 | BRV | 0 | 0 | ++ | 0 |
| 4 | 275-295C | ND | ND | ++++ | +++ |
| 5 | 275-295C-KLH | 0 | + | ++++ | ++ |
| 6 | VP6-(C275-295) | 0 | 0 | ++++ | + |
| 7 | VP6-(BP-275-295) | ++ | 0 | +++ | ++ |

ND = Not done; baby mice were cannibalized by mother.

As shown in Table 5, protection was not achieved with respect to the SA11 serotype, even with whole BRV virus. However, in strains Wa and DS-1, where whole BRV virus was protective, excellent protection was achieved using the 275–295 peptide, especially when conjugated to the VP6 or KLH carrier. Protection was also shown, though to a less complete extent, against challenge by BRV.

TABLE 6

Protection Against Infection (Xylose Absorption)

| Groups | Immunogen | Wa | DS-1 | SA-11 | BRV |
| --- | --- | --- | --- | --- | --- |
| 1 | Placebo | 65 | 63 | 54 | 60 |
| 2 | VP6 | 68.6 | 67.2 | 58 | 63.7 |
| 3 | BRV | 110 | 112 | 69 | 118 |
| 4 | 275-295C | ND | 60 | 53 | 59 |
| 5 | (275-295C)-KLH | ND | 80 | 55 | 65 |
| 6 | VP6 (275-295) | 119 | 114 | 56 | 78 |
| 7 | VP6-(BP-275-295) | 89 | 102 | 59 | 65 |
| | Non-challenged Control | 118 | 119 | 119 | 120 |

These results were confirmed using the xylose absorption assay as shown in Table 6. The levels of plasma xylose shown after challenge with the various viral strains for the VP6/BP-photo-275–295 conjugate are essentially identical to those achieved by vaccination with whole BRV. Again, the simian strain SA11 does not show cross-reactivity.

EXAMPLE 7

Subunit Vaccines Derived from VP4

The trypsin cleavage site of VP4 was identified at the location shown boxed in FIG. 2 by taking advantage of the known amino acid sequence of the protein, the nature of trypsin specificity, and the size of the fragments resulting from trypsin cleavage. According to these criteria, positions 232–255 inclusive were identified as comprising the trypsin cleavage site.

As shown in the figure, the sequence shown at the location of positions 232–235 in both the bovine C486 strain and the simian SA11 strain are identical; the position notations reflect those shown in the figure as the sequences are there disposed.

As seen in FIG. 2, the amino acid sequence in these positions of C486 strain and simian SA11 strain is Asn-Ile-Val-Pro-Val-Ser-Ile-Val-Ser-Arg-Asn-Ile-Val-Tyr-Thr-Arg-Ala-Gln-Pro-Asn-Gln-Asp-Ile-Val (position 229–252 of SEQ ID NO:16). If a synthetic peptide is constructed wherein Ala is substituted for all of the Val residues, the sequence of this peptide would be Asn-Ile-Ala-Pro-Ala-Ser-Ile-Ala-Ser-Arg-Asn-Ile-Ala-Tyr-Thr-Arg-Ala-Gln-Pro-Asn-Gln-Asp-Ile-Ala (SEQ ID NO:21).

A synthetic peptide designed to mimic this sequence but having some substitutions for ease of synthesis was constructed as follows:

Asn-Ile-Ala-Pro-Ala-Ser-Ile-Val-
Ser-Arg-Asn-Ile-Val-Tyr-Thr-Arg-
Ala-Gln-Pro-Asn-Asp-Ile-Ala (positions 2–25 of
SED ID NO. 7).

The synthesized protein also was extended with N-terminal cysteine not present in the native protein for ease in conjugation to carrier (SEQ ID No. 7). These peptides have substitutions of alanine for valines at positions 234, 236 and 255 of the native VP4 in FIG. 2 as shown. It is believed that valine and alanine are interchangeable at these positions with respect to the behavior of the peptide biologically.

For use as an immunogen, the synthetic peptide described was coupled to KLH and to VP6. The conjugation to KLH is conducted through the cysteine at the N-terminus under the protocol described for VP7 peptide in Example 5 above. The conjugate is designated KLH-(232–255).

The coupling of the 232–255 peptide to VP6 was conducted by protein-protein interaction. The VP4 subunit peptide has the properties of a binding peptide intrinsically, shown as follows.

When 100 μg of the peptide was reacted with 2 μg purified virus for 30 minutes at 37° C., the VP6 45 kd capsid protein from the virus showed a laddering effect upon polyacrylamide gel electrophoresis; at 25 μg of the peptide, the laddering was not apparent. Laddering occurred both at the VP6 monomeric molecular weight of 45 kd and at the aggregate molecular weights of 90 kd and 135 kd regions. The increment in the ladder steps matched the MW of the 232–255 peptide. Trypsin treatment of the virus/peptide complex reduced the ladder to a virus profile identical with that of the trypsin-treated virus. The ladder could be detected with antisera produced against the synthetic peptide.

The 232–255 VP4 synthetic peptide maintained its reactivity with VP6 under conditions where samples were treated with urea sample buffer for 30 minutes at 37° C., and when samples were treated with Laemmli buffer without β-mercaptoethanol (BME) but with boiling. However, when BME was included in the sample buffer and the sample was boiled prior to electrophoresis, the ladders in both the 45 kd and 90 kd regions disappeared. Thus, secondary structure specified by disulfide bridging is apparently necessary to maintain the complex.

The 232–255 VP4 peptide was mixed with the VP6 carrier prepared as described above in 0.1 M PBS, pH 6.5, for 30 minutes at 37° C. The weight ratio of peptide to carrier was 10:1 (w/w). The resulting conjugates were designated VP6-(232–255).

The KLH conjugate, prepared as described above, was initially used in standard immunization protocols in mice and the 50% plaque reduction assay described above was used to determine the neutralizing ability of the resulting antiserum. A 50% reduction in plaques occurred at a 5000-fold dilution of the resultant antiserum. A 10,000-fold dilution of monoclonal antibody immunoreactive with the synthetic peptide also showed 50% plaque reduction.

In addition to testing for neutralization, the ability of the VP4 subunit peptide to protect against infection was assessed as described for the VP7 subunit peptides in Example 6. The conjugates were administered at 50 µg dosages emulsified with Freund's Complete Adjuvant in the primary immunization and with Freund's Incomplete Adjuvant in the second and third immunizations conducted at 2-week intervals. The antisera produced reacted specifically both with reduced and nonreduced VP4. Both VP6-(232–255) and KLH-(232–255) showed complete protection against infection as measured by clinical (diarrhea) data with respect to the Wa and DS-1 strains. The VP6 conjugate also showed complete protection against BRV and SA11 infection. Partial protection was shown in these strains by the KLH conjugate. Furthermore, when mixed with VP6-(BP275–295), VP6-(232–255) gave complete protection with respect to all strains. These data were confirmed by the D-xylose adsorption assay, as shown by the results in Table 7.

TABLE 7

Protection Against Infection (Xylose Adsorption)
Plasma D-Xylose Concentration
(µg/100 ml) Following Challenge
with Rotavirus Isolate*

| Groups | Immunogen | Wa | DS-1 | SA11 | BRV |
|---|---|---|---|---|---|
| 10 | KLH-(232-255) | 110 | 114 | 70 | 77 |
| 11 | VP6-(232-255) | 112.5 | 110 | 108 | 113 |
| 12 | VP6(232-255) + VP6 BP (275-295) | 117 | 111 | 109 | 119 |
|  | Non-challenged Control | 118 | 119 | 119 | 120 |

As shown in Table 7, the VP6-(232–255) conjugate gave complete protection against infection by all strains.

EXAMPLE 8

Therapeutic Activity of the VP4 Subunit (232–255)

Susceptibility of the synthetic peptide to trypsin was confirmed by reaction with trypsin followed by electrophoresis. The peptide was shown to be cleaved by trypsin in a dose-dependent manner. It was also established that the peptide could compete with intact VP4 for the enzyme. This was determined by measuring the ability of increasing concentrations of the synthetic peptide to reduce the amount of VP4 cleaved into the two products of molecular weight 60 kd and 28 kd. As shown in FIG. 8, increasing amounts of synthetic peptide provided protection against VP4 cleavage. Initially, trypsin was used in a quantity which resulted in complete cleavage of VP4 (25 µg (232–255)/25 µg VP4); when the synthetic peptide was increased to 200 µg, intact VP4 is evident.

The 232–255 VP4 peptide was also capable of plaque reduction in a dose-dependent manner when mixed with infectious virus. In a protocol similar to a standard plaque reduction assay, MA104 cells were treated with 100 pfu of the virus in the absence of and in the presence of 100 µg, 200 µg and 300 µg of the 232–255 peptide. At high concentrations of the peptide, plaques were seen in the test wells only 5–6 days after plaques in the control wells were seen, and were very small and diffuse.

EXAMPLE 9

Prophylactic Activity of the VP4 Subunit (232–255)

The 232–255 peptide synthesized in Example 7 was diluted serially in Eagle's Minimal Essential Medium. The peptide solutions of various dilutions were administered in 100 µl dosages to neonatal mice by oral administration. The pups were born of rotavirus-free strain CD-1 dams and administration was at 7 days of age (when the pups weigh about 4 g). Approximately one hour later the mice were challenged with $10^4$ pfu of BRV strain C486. Clinical protection was scored as described in Example 6. Diarrhea was scored clinically as well as on necropsy, and plasma D-xylose was determined by administering 100 µl of 5% w/v D-xylose solution, sacrificing the mice two hours later, collecting the blood and determining plasma D-xylose concentration as described above. Virus titers were determined in the mouse intestines by suspending in MEM and homogenizing for virus titration. Mice which received no challenge had plasma D-xylose levels of 119 µg/100 µl and zero viral titers. The results are shown in Table 8.

TABLE 8

Passive Protection by 232-255 of VP4

| Peptide Administered (µg) | Diarrheal Score | Plasma D-Xylose (µg/100 µl) | Virus Titre (PFU/ml) |
|---|---|---|---|
| 100 | +++ | 92 | $1.2 \times 10^3$ |
| 250 | ++ | 70 | $4.0 \times 10^2$ |
| 500 | 0 | 101 | 0 |
| 1000 | 0 | 112 | 0 |
| 0 | ++++ | 57 | $5 \times 10^3$ |

As shown in Table 8, administered peptides in the amount of 500–1000 µg completely protected the mice against viral infection.

EXAMPLE 10

VP4 Subunit Vaccine 240–248

A contracted subunit of the VP4 peptide 232–255 of the foregoing examples was synthesized using solid phase synthesis. This peptide corresponds to amino acids 240–248 of BRV strain C486 with an N-terminal extension to facilitate conjugation to carrier. Thus, the peptide has the amino acid sequence: Cys-Gly-Ala-Ser-Arg-Asn-Ile-Val-Tyr-Thr-Arg-Ala. (SEQ ID NO:8)

The Cys-Gly-Ala at the N-terminus contains a Gly-Ala spacer and an N-terminal cysteine. This peptide was purified using reverse-phase HPLC before conjugation to carrier.

VP6 carrier was prepared and induced to form spheres as described hereinabove in Example 5. Conjugation to carrier was effected by protein-protein interaction wherein the VP6 carrier protein and the peptide were mixed at 1:10 (w/w) carrier:peptide ratio in 0.1 M PBS, pH 7.4 and incubated for 30 min. at 37° C. The resulting conjugate was verified by SDS-PAGE.

The conjugates were used in an immunization protocol in mouse dams as described in the mouse immunization portion of Example 6. Suckling seven-day-old mice from the immunized dams were challenged with rotavirus isolates at $10^4$ pfu per mouse and the morbidity and mortality were scored clinically as described; the intestinal dysfunction induced post-rotavirus infection was assessed by D-xylose absorption and the protection scores are based on both clinical scores and plasma D-xylose concentration.

C, or complete protection, corresponds to zero clinical score and xylose greater than 100 μg/100 μl;

P, or partial protection, corresponds to less than ++ clinical score and xylose greater than 10 μg/100 μl; and N, or no protection, corresponds to greater than ++ clinical score and xylose concentration less than 60 μg/100 μl plasma.

The results of this protocol with respect to several rotavirus strains are shown in Table 9.

TABLE 9

Protection by VP4 240-248 Conjugate

| | Wa | DS-1 | SA-11 | BRV |
|---|---|---|---|---|
| Placebo | N | N | N | N |
| VP6 | P | P | N | P |
| BRV | C | C | P | C |
| VP6-(240-248) | C | C | P | C |

As seen in Table 9, complete protection was obtained with respect to strains Wa, DS-1 and BRV. The subunit provides comparable protection to that provided by the whole virus and better than that provided by carrier VP6 alone.

EXAMPLE 11

Therapeutic Activity of VP4 240–248

The peptide synthesized in Example 10 representing positions 240–248 of VP4 was shown to be effective in preventing plaque formation by rotavirus in permissive cells. The plaque assay was that described by Aha and Sabara, *J Virol Methods* (1990) 28:25–32, modified as follows. Replicate cultures of MA-104 cells were incubated with dilutions of peptide ranging from 30–600 μg/ml for 1 hr at 37° C. and the remainder of the assay was conducted as described in the reference. The results showed that the VP4 240–248 peptide was effective in preventing plaque formation.

Furthermore, the 240–248 peptide blocks the attachment of rotavirus to susceptible cells. Bovine rotavirus strain C486 was produced in tissue culture by infection of MA-104 cells. The infected cells were pulsed for 1 hr with 25 μCi of $^{35}$S-labeled methionine and infection was allowed to proceed. The virus was then purified and concentrated by centrifugation in a sucrose gradient as described by Sabara et al., *J Virol* (1985) 56:1037–1040.

Replicate cultures of MA-104 cells were incubated with dilutions of peptides ranging from 30–600 μg/ml for 1 hr at 37° C. As above, the peptide control derived from gp gI was included with the dilution range. Cells were then washed with MEN and a total of 0.045 μCi ($10^4$ cpm) of $^{35}$S-labeled virus was added to each culture. After incubation for 1 hr at 37° C. in a humidified atmosphere containing 5% $CO_2$, the cells were washed thoroughly and solubilized in 0.1 M PBS, pH 7.4 containing 0.1% SDS, 0.5% Nonidet P40, and 0.5% sodium deoxycholate. The samples were prepared for scintillation counting and incorporation of a radiolabel into the cultures was determined.

The results showed that samples incubated with at least 30 μg (total) (300 μg/ml dilution) of the peptide showed essentially no uptake of labeled virus.

Finally, hemagglutinating activity was measured using a modification of the method described by Kalica et al., *J Clin Microbiol* (1978) 7:314–315. (VP4 is believed to be the rotavirus hemagglutinating protein required for attachment.) Two-fold dilutions of the peptide were prepared with the starting concentration of 500 μg/ml and human group O Rhesus-positive erythrocytes were added to each sample to produce a final concentration equivalent to 0.4% packed cell volume. After incubation for 2 hr, the tests were scored for agglutination. Peptide 240–248 was found to produce hemagglutination at 500 μg/ml. Thus, the peptide may be an effective diluent of VP4 activity in situ.

EXAMPLE 12

VP6-Derived Subunit Vaccine

A subunit of the VP6 rotavirus protein was designed based on amino acid positions 40–60 inclusive. FIG. 3 shows the amino acid sequence of the VP6 protein of the strain SA11. The peptide corresponding to this subunit, modified to facilitate coupling was synthesized using standard solid phase techniques and has the structure:

```
Thr-Met-Asn-Gly-Asn-Glu-Phe-Gln-Thr-Gly-Gly-
Ile-Gly-Asn-Leu-Pro-Ile-Arg-Asn-Trp-Asn-Gly-Cys. (SEQ ID NO: 9)
```

The Gly-Cys at the C-terminus is added to provide a linkage site.

The synthesized peptide itself was reactive in an ELISA with anti-VP6 monospecific serum and with several monoclonal antibodies known to be immunoreactive with the VP6 protein. These monoclonals, designated 1D7, 1B4, 1B9 and 1D10 were mildly neutralizing in a plaque reduction assay and were immunoreactive with the 40–60 peptide at reciprocal dilutions of 5,000–8,000.

To test the immunogenicity and protective effect of the 40–60 VP6 peptide, the peptide was conjugated to KLH and E. coli pilin protein K99 using the procedures set forth above with respect to the VP7 subunit. Both conjugates were capable of raising significant anti-rotavirus ELISA titers after several immunizations. In addition, these conjugates were shown to be protective in mice. Female mice were immunized three times during a schedule of breeding and pregnancy wherein the last immunization was given two weeks prior to whelping, as described above. Immunizations were conducted using 100 μg immunogen in the presence of either Freund's Complete Adjuvant, or dimethyl dioctadecyl ammonium bromide (DDA) adjuvant. The mouse pups were allowed to suckle and challenged at 7 days with bovine rotavirus. Morbidity, mortality and severity of diarrhea were scored over a 48 hour period following challenge; most diarrhea and morbidity was apparent within 3–5 hours following challenge.

Using the scoring system set forth above, (40–60)-KLH using FCA as adjuvant gave some protection as did K99-(40–60) in the presence of FCA (diarrhea score +, as compared to ++++ in KLH controls). K99-(40–60) in the presence of DDA gave almost complete protection by these criteria.

Finally, the VP6 40–60 subunit was tested for its ability to protect neonates against challenge in the same protocols described above with respect to the VP7 and VP4 subunits. The KLH-(40–60) conjugate was used in the same experiments for which the results are reported in Tables 5 and 6 above. The KLH-(40–60) results are shown in Table 10.

TABLE 10

|  | Wa | DS-1 | SA11 | BRV |
| --- | --- | --- | --- | --- |
| Diarrhea Score |  |  |  |  |
| KLH-(40-60) | + | + | ++++ | ++ |
| Negative Control | +++ | +++ | ++++ | ++++ |
| BRV | 0 | 0 | ++ | 0 |
| Xylose Absorption |  |  |  |  |
| KLH-(40-60) | 74 | 81 | 53 | 64 |
| Negative Control | 65 | 63 | 54 | 60 |
| BRV | 110 | 112 | 69 | 118 |
| Nonchallenged Control | 118 | 119 | 119 | 120 |

As shown in Table 10, the KLH conjugated 40–60 peptide gives partial protection to challenge by Wa and DS-1 strains, but little or no protection with respect to SA11 and BRV, as judged by clinical criteria. These results are consistent with those obtained using xylose absorption.

EXAMPLE 13

Effect of Carrier and Adjuvant

The KLH carrier (approximately 3500 kd) and K99 (approximately 19 kd) were compared using the VP7 275–295 subunit and the VP6 40–60 subunit. The conjugates were prepared through an N-terminal cysteine in each case. Mice were immunized with 100 μg of the KLH and K99 conjugates of these peptides in an immunization protocol involving three immunizations. Table 11 shows the antibody titers against rotavirus of mice which were seronegative at the time of immunization. As shown in the table, the use of either KLH or K99 as a carrier gave comparable results, although K99 appeared to be slightly more immunogenic with respect to 40–60.

TABLE 11

Anti-Rotavirus ELISA Titers Following Immunization

| Peptide | Carrier | 2 Weeks Post 1st Immunization | 2 Weeks Post 2nd Immunization | 2 Weeks Post 3rd Immunization |
| --- | --- | --- | --- | --- |
| VP6-40-60 | KLH | 1,333 | 13,335 | 42,170 |
|  | K99 | 13,335 | 31,623 | 74,990 |
| VP7-275-295 | KLH | 4,870 | 42,170 | 56,234 |
|  | K99 | 7,500 | 23,713 | 56,234 |

The effect of adjuvant was also tested, in comparing Freund's Complete Adjuvant (FCA) and dimethyl dioctadecyl ammonium bromide (DDA). The K99 conjugate with the VP7 275–295 subunit was tested on seronegative mice using 100 μg of conjugate with either 0.1 ml FCA or 100 μg DDA. The results are shown in Table 12; both adjuvants resulted in obtaining significant antirotaviral titers two weeks after the second immunization. These levels are comparable to those obtained using immunization with virus per se, without carrier which gave an ELISA rotavirus titer of 15,850 two weeks post-second immunization. The ability of the peptide to raise anti-rotavirus titers was dose-dependent; 1 μg and 10 μg immunizations did not provide significant anti-rotavirus titers.

TABLE 12

ELISA Titers Following Immunization

| Adjuvant |  | Two Weeks Post First Immunization | Two Weeks Post Second Immunization |
| --- | --- | --- | --- |
| Freund's Complete Adjuvant | Anti-rota | 9 | 6,310 |
|  | Anti-K99 | 31,600 | 50,120 |
| Dimethyl dioctadecyl Ammonium Bromide | Anti-rota | 89 | 7,495 |
|  | Anti-K99 | 251,200 | 10,000,000 |

We claim:

1. An isolated peptide useful as an immunochemical which peptide consists of the amino acid sequence of positions 40–60 of the rotavirus VP6 viral protein optionally modified to facilitate conjugation.

2. The isolated peptide of claim 1 wherein said modification further consists of a cysteine extension at the N-terminus or C-terminus of the peptide.

3. The isolated peptide of claim 1 wherein the amino acid sequence is Thr-Met-Asn-Gly-Asn-Glu-Phe-Gln-Thr-Gly-Gly-Ile-Gly-Asn-Leu-Pro-Ile-Arg-Asn-Trp-Asn-Gly-Cys (SEQ ID NO:9).

4. The isolated peptide of claim 1 wherein said amino acid sequence is Thr-Met-Asn-Gly-Asn-Glu-Phe-Gln-Thr-Gly-Gly-Ile-Gly-Asn-Leu-Pro-Ile-Arg-Asn-Trp-Asn (SEQ ID NO:24).

5. A peptide immunochemical composition comprising the peptide of claim 1 further conjugated to a carrier.

6. The peptide immunochemical composition of claim 5 wherein said carrier is keyhole limpet hemocyanin (KLH), K99 pilin protein, or VP6.

7. The peptide immunochemical composition of claim 6 wherein the carrier is KLH.

8. An immunochemical composition to initiate an antibody response in a mammalian or avian subject against rotavirus which composition comprises an effective amount of the peptide of claim 1 or said peptide conjugated to a carrier to stimulate antibody production in admixture with a pharmaceutically acceptable excipient.

9. A method to initiate an antibody response in a mammalian or avian subject against rotavirus, which method comprises administering to a subject an effective amount of the peptide of claim 1 or said peptide conjugated to a carrier to stimulate antibody production.

10. An isolated protein having an antigenic determinant in the amino acid sequence of positions 40–60 of rotavirus VP6.

11. The isolated protein of claim 10 wherein said amino acid sequence is contained at least twice in said protein.

12. An immunochemical composition to initiate an antibody response in a mammalian or avian subject against rotavirus which composition comprises an effective amount of the protein of claim 10 or said protein conjugated to a carrier to stimulate antibody production in admixture with a pharmaceutically acceptable excipient.

13. A method to initiate an antibody response in a mammalian or avian subject against rotavirus, which method comprises administering to a subject an effective amount of the protein of claim 10 or said protein conjugated to a carrier to stimulate antibody production.

14. An isolated peptide useful as an immunochemical, which peptide consists of the amino acid sequence of positions 232–255 of the rotavirus VP4 viral protein or said amino acid sequence wherein one or more of the valine residues natively occurring in said sequence at any of positions 234, 236 or 255 is substituted by an alanine, said peptide optionally modified to facilitate binding to a carrier.

15. The isolated peptide of claim 14 wherein said modification further consists of a cysteine extension at the N-terminus or C-terminus of the peptide.

16. The isolated peptide of claim 14 wherein said amino acid sequence is Cys-Asn-Ile-Ala-Pro-Ala-Ser-Ile-Val-Ser-Arg-Asn-Ile-Val-Tyr-Thr-Arg-Ala-Gln-Pro-Asn-Gln-Asp-Ile-Ala (SEQ ID NO:7).

17. The isolated peptide of claim 14 wherein said amino acid sequence is Asn-Ile-Ala-Pro-Ala-Ser-Ile-Val-Ser-Arg-Asn-Ile-Val-Tyr-Thr-Arg-Ala-Gln-Pro-Asn-Gln-Asp-Ile-Ala (SEQ ID NO:23).

18. The isolated peptide of claim 14 wherein said amino acid sequence is Asn-Ile-Val-Pro-Val-Ser-Ile-Val-Ser-Arg-Asn-Ile-Val-Tyr-Thr-Arg-Ala-Gln-Pro-Asn-Gln-Asp-Ile-Val (SEQ ID NO:22).

19. A peptide immunochemical composition comprising the peptide of claim 14 conjugated to a carrier.

20. The peptide immunochemical composition of claim 19 wherein said carrier is keyhole limpet hemocyanin (KLH) or K99 pilin protein.

21. The peptide immunochemical composition of claim 20 wherein the carrier is KLH.

22. An immunochemical composition to initiate an antibody response in a mammalian or avian subject against rotavirus which composition comprises an effective amount of the peptide of claim 14 or said peptide conjugated to a carrier to stimulate antibody production in admixture with a pharmaceutically acceptable excipient.

23. A method to initiate an antibody response in a mammalian or avian subject against rotavirus, which method comprises administering to a subject an effective amount of the peptide of claim 14 or said peptide conjugated to a carrier to stimulate antibody production.

24. An isolated protein, which protein has an antigenic determinant in the amino acid sequence of positions 232–255 of rotavirus VP4 or said amino acid sequence as modified by replacing at least one valine of the native sequence at any of positions 234, 236 or 255 by an alanine residue.

25. The isolated protein of claim 24 wherein said amino acid sequence is contained at least twice in said protein.

26. An immunochemical composition to initiate an antibody response in a mammalian or avian subject against rotavirus which composition comprises an effective amount of the protein of claim 24 or said protein conjugated to a carrier to stimulate antibody production in admixture with a pharmaceutically acceptable excipient.

27. A method to initiate an antibody response in a mammalian or avian subject against rotavirus, which method comprises administering to a subject an effective amount of the protein of claim 24 or said protein conjugated to a carrier to stimulate antibody production.

28. A method to initiate an antibody response in a subject, which method comprises administering to a subject an effective amount of the peptide of claim 14 to stimulate antibody production.

29. A method to initiate an antibody response against rotavirus, which method comprises administering to a subject an effective amount of the protein of claim 24 to stimulate antibody production.

30. A method to initiate an antibody response against rotavirus in a subject, which method comprises orally administering to a subject an effective amount of the peptide of claim 14 to stimulate antibody production.

31. A method to initiate an antibody response against rotavirus in a subject, which method comprises orally administering to a subject an effective amount of the protein of claim 24 to stimulate antibody production.

32. An isolated peptide useful as an immunochemical which peptide consists of the amino acid sequence of positions 240–248 of the rotavirus VP4 viral protein optionally modified to facilitate coupling to a carrier, said peptide or modified peptide being coupled covalently to said carrier and said carrier being other than VP6.

33. The isolated peptide of claim 32 wherein said carrier is keyhole limpet hemocyanin (KLH) or K99 pilin protein.

34. The isolated peptide of claim 32 wherein said amino acid sequence is Ser-Arg-Asn-Ile-Val-Tyr-Thr-Arg-Ala (SEQ ID NO:20).

35. An immunochemical composition to initiate an antibody response in a mammalian or avian subject against rotavirus infection which composition comprises an effective amount of the peptide conjugated to a carrier of claim 32 to stimulate antibody production in admixture with a pharmaceutically acceptable excipient.

36. A method to initiate an antibody response in a mammalian or avian subject against a rotavirus, which method comprises administering to a subject an effective amount of the peptide conjugated to a carrier of claim 32 to stimulate antibody production.

37. An isolated protein having antigenic determinant in the amino acid sequence of positions 240–248 of rotavirus VP4 where said amino acid sequence is contained at least twice in said ptotein.

38. An immunochemical composition to initiate an antibody response in a mammalian or avian subject against rotavirus composition for vaccine comprises an effective amount of the protein of claim 37 or said protein conjugated to a carrier to stimulate antibody production in admixture with a pharmaceutically acceptable excipient.

39. A method to initiate an antibody response in a mammalian or avian subject against roravirus, which method comprises administering to a subject an effective amount of the protein of claim 37 or said protein conjugated to a carrier to stimulate antibody production.

* * * * *